US011432990B2

(12) United States Patent
Christoforou et al.

(10) Patent No.: US 11,432,990 B2
(45) Date of Patent: Sep. 6, 2022

(54) TEXTURED APPARATUS WITH THERAPEUTIC MATERIAL INCORPORATED THEREIN AND METHODS OF MANUFACTURING SAME

(71) Applicant: ISOS Solutions, LLC, Brooklyn, NY (US)

(72) Inventors: Dimitrios Christoforou, Nissequogue, NY (US); Vipul Patel, New York, NY (US)

(73) Assignee: ISOS Solutions, LLC, Brooklyn, NY (US)

( * ) Notice: Subject to any disclaimer, the term of this patent is extended or adjusted under 35 U.S.C. 154(b) by 819 days.

(21) Appl. No.: 16/359,425

(22) Filed: Mar. 20, 2019

(65) Prior Publication Data

US 2019/0209420 A1   Jul. 11, 2019

Related U.S. Application Data

(63) Continuation-in-part of application No. 14/474,751, filed on Sep. 2, 2014, now abandoned.
(Continued)

(51) Int. Cl.
*A61H 7/00* (2006.01)
*A61H 1/00* (2006.01)

(52) U.S. Cl.
CPC ............ *A61H 7/003* (2013.01); *A61H 1/00* (2013.01); *A61H 2201/165* (2013.01);
(Continued)

(58) Field of Classification Search
CPC .......... A61H 7/00; A61H 7/001; A61H 7/002; A61H 7/003; A61H 7/004; A61H 7/005;
(Continued)

(56) References Cited

U.S. PATENT DOCUMENTS 1,261,706 A   4/1918  Condley
1,795,500 A   3/1931  Omundson
(Continued)

FOREIGN PATENT DOCUMENTS

CN   203169818 U   9/2013
CN   203379477 U   1/2014
(Continued)

OTHER PUBLICATIONS

English translation for KR 20060057136, machine translated through Search engine and by Clarivate Analytics, translated on Apr. 8, 2022.*
(Continued)

*Primary Examiner* — Tu A Vo
(74) *Attorney, Agent, or Firm* — Intrinsic Law Corp.

(57) ABSTRACT

A device that fits on a person's finger to reduce the effect, appearance, and/or sensitivity of a scar. The device includes a therapeutic material such as a therapeutic cream that can be released upon the application of heat such as frictional heat generated during use of the device. The device can also be used as an applicator to distribute and work therapeutic material into the scar after the therapeutic material has been placed directly onto the scar tissue. A method of manufacturing the device includes mixing the therapeutic material, a moldable material, and an optional curing agent to form a compound material, molding the compound material, heating the compound material or the molded structure, and curing the molded structure. Alternatively, the curing agent can be absorbed into the cured structure.

16 Claims, 16 Drawing Sheets

Related U.S. Application Data

(60) Provisional application No. 61/872,007, filed on Aug. 30, 2013.

(52) U.S. Cl.
CPC ............... *A61H 2201/1635* (2013.01); *A61H 2201/1692* (2013.01); *A61H 2205/067* (2013.01)

(58) Field of Classification Search
CPC .................. A61H 7/007; A61H 7/008; A61H 2201/1692; A61H 2201/1695; A61H 2205/067; A46B 5/322; A46B 2200/10; A46B 2200/1006; A46B 2200/102; A41D 13/087; A41D 19/01517
See application file for complete search history.

(56) References Cited

U.S. PATENT DOCUMENTS

| | | | |
|---|---|---|---|
| 1,965,009 A | 7/1934 | Stevens | |
| 2,018,903 A | 10/1935 | Stevens | |
| 2,075,681 A | 3/1937 | Logue | |
| 2,077,540 A | 4/1937 | Logue | |
| 2,103,083 A | 12/1937 | Lynch | |
| 2,686,325 A | 8/1954 | Silver | |
| 2,717,799 A | 9/1955 | Jones | |
| 4,249,521 A | 2/1981 | Gueret | |
| 4,308,860 A | 1/1982 | Sanders | |
| 4,372,296 A | 2/1983 | Fahim | |
| 4,628,949 A | 12/1986 | Mas | |
| 4,766,915 A | 8/1988 | Ficke | |
| 5,213,428 A | 5/1993 | Salman | |
| 5,287,584 A * | 2/1994 | Skinner | A46B 5/04 2/21 |
| 5,392,482 A | 2/1995 | Drulias | |
| D363,606 S | 10/1995 | Abrahamson | |
| 5,735,804 A | 4/1998 | Chan | |
| 5,741,509 A | 4/1998 | Kushner | |
| 5,765,252 A | 6/1998 | Carr | |
| 6,030,374 A | 2/2000 | McDaniel | |
| 6,110,186 A | 8/2000 | Rizvi | |
| D430,677 S | 9/2000 | Robinson | |
| 6,534,693 B2 | 3/2003 | Fischell | |
| D495,803 S | 9/2004 | Gough | |
| 7,628,764 B2 | 12/2009 | Duarte | |
| D615,304 S | 5/2010 | Roher | |
| 7,707,654 B1 | 5/2010 | Spence | |
| 7,743,690 B2 | 6/2010 | White | |
| D669,996 S | 10/2012 | Chen | |
| 8,376,984 B2 | 2/2013 | James | |
| 8,523,791 B2 | 9/2013 | Castel | |
| 8,549,693 B2 | 10/2013 | Gruber | |
| D693,934 S | 11/2013 | Lin | |
| 8,622,890 B1 | 1/2014 | Caggiano | |
| D705,940 S | 5/2014 | Tai | |
| 8,970,558 B1 | 3/2015 | Gore | |
| 2003/0088930 A1 | 5/2003 | Abada | |
| 2003/0212350 A1 | 11/2003 | Tadlock | |
| 2004/0044328 A1* | 3/2004 | Kemp | A61H 19/34 604/500 |
| 2006/0110415 A1 | 5/2006 | Gupta | |
| 2007/0118947 A1 | 5/2007 | Lorenzo | |
| 2007/0118963 A1 | 5/2007 | Snyder | |
| 2008/0058648 A1 | 3/2008 | Novak | |
| 2008/0071203 A1 | 3/2008 | Miller | |
| 2009/0259168 A1 | 10/2009 | Prizant | |
| 2011/0107499 A1 | 5/2011 | Jeong | |
| 2011/0230817 A1 | 9/2011 | Moy | |
| 2011/0230870 A1 | 9/2011 | Moy | |
| 2013/0012858 A1 | 1/2013 | Jackson | |
| 2013/0060166 A1 | 3/2013 | Friedman | |
| 2013/0079689 A1 | 3/2013 | Thierman | |
| 2014/0142522 A1 | 5/2014 | Filippova | |
| 2015/0224025 A1* | 8/2015 | Darna | A61H 39/04 606/204 |
| 2016/0004508 A1 | 1/2016 | Elmer | |
| 2016/0045081 A1 | 2/2016 | Kern | |

FOREIGN PATENT DOCUMENTS

| | | | |
|---|---|---|---|
| EP | 0651628 B1 | 5/1995 | |
| EP | 1448263 B1 | 8/2004 | |
| GB | 398919 A | 9/1933 | |
| KR | 20060057136 A * | 5/2006 | ............ A45D 44/22 |
| WO | 199304691 A1 | 3/1993 | |
| WO | 9952488 A2 | 10/1999 | |
| WO | 2003086535 A1 | 10/2003 | |
| WO | 2006040597 A1 | 4/2006 | |
| WO | 2007139812 A2 | 12/2007 | |
| WO | 2011006100 A1 | 1/2011 | |
| WO | 2011116135 A1 | 9/2011 | |

OTHER PUBLICATIONS

Dow Corning, "Dow Corning QP1-30 Silicone Elastomer", Product Information Healthcare, Oct. 29, 2013, p. 1-3, Dow Corning Corporation.

Dow Corning, "Step-By-Step Production Selection Guide", Xiameter from Dow Corning, 2014, p. 1-8, Dow Corning Corportation.

Dow Corning, "Moulding of Silastic Silicone Rubber", Date Unknown, p. 3-12, Dow Corning Corportation.

"Region" definition, dictionary.com, Sep. 14, 2017.

"Along" definition, dictionary.com, Sep. 14, 2017.

"Coarse" definition, dictionary.com, Sep. 14, 2017.

"Treat" definition, Oxfordictionaries.com, Sep. 14, 2017.

R. Connery, "Ultrasound Scar Removal", eHow, Date Unknown.

Huang et al., "Pressure therapy upregulates matrix metalloproteinase expression and downregulates collagen expression in hypertrophic scar tissue", Chin. Med. J., 2013, p. 3321-3324, vol. 126, issue 17.

Tan et al., "Effects of pressure therapy on the proliferation and apoptosis of cells in hypertrophic scar of burn patients", Zhonghua Shao Shang Za Zhi, 2013, p. 509-515, vol. 26, issue 6.

Li et al., "Detection of changes of scar thickness under mechanical loading using ultrasonic measurement", Burns, Feb. 2013, p. 89-97, vol. 39, issue 1.

Van Der Veer et al., "Potential cellular and molecular causes of hypertrophic scar formation", Burns, Feb. 2009, p. 15-29, vol. 35, issue 1.

Costa et al, "Mechanical Forces Induce Scar Remodeling: Study in Non-Pressure-Treated versus Pressure-Treated Hypertrophic Scars", The American Journal of Pathology, Nov. 1999, p. 1671-1679, vol. 155, issue 5.

Gurtner et al., "Improving Cutaneous Scar Formation by Controlling the Mechanical Environment: Large Animal and Phase I Studies", Annals of Surgery, Aug. 2011, p. 217-225, vol. 254, issue 2.

Junker et al., "Assessing quality of healing in skin: Review of available methods and devices", Wound Repair and Regeneration, May 2014, p. 2-10, vol. 22, issue S1, Wound Healing Society.

Kwan et al., "Scar and Contracture: Biological Principles", Hand Clin., Nov. 2009, p. 511-528, vol. 25, issue 4.

R. Ogawa, "Mechanobiology of scarring", Wound Repair and Regeneration, Sep./Oct. 2011, p. s2-s9, vol. 19, issue S1, Wound Healing Society.

Reno et al., "In vitro mechanical compression induces apoptosis and regulates cytokines release in hypertrophic scars", Wound Repair and Regeneration, Sep. 2003, p. 331-336, vol. 11, issue 5.

Reno et al., "Effects of mechanical compression on hypertrophic scars: prostaglandin E2 release", Burns, May 2001, p. 215-218, vol. 27, issue 3, Elsevier Science Ltd.

Van Den Helder et al., "Sense and Nonsense of Scar Creams and Gels", Aesthetic Plastic Surgery, Summer 1994, p. 307-313, vol. 18, issue 3.

(56) References Cited

OTHER PUBLICATIONS

A. D. D Widgerow, "Cellular/extracellular matrix cross-talk in scar evolution and control", Wound Repair and Regeneration, Mar./Apr. 2011, p. 117-133, vol. 19, issue 2, Wound Healing Society.
A. D. Widgerow, "Current Concepts in Scar Evolution and Control", Aesthetic Plastic Surgery, Aug. 2011, p. 628-635, vol. 35, issue 4, Springer Science & Business Media, LLC and International Society of Aesthetic Plastic Surgery.
Widgerow et al., "New Innovations in Scar Management", Aesthetic Plastic Surgery, May 2000, p. 227-234, vol. 24, issue 3.
Definition for the term "along", Dictionary.com, captured on Dec. 17, 2018.

* cited by examiner

TEXTURED APPARATUS WITH THERAPEUTIC MATERIAL INCORPORATED THEREIN AND METHODS OF MANUFACTURING SAME

CROSS-REFERENCE TO RELATED APPLICATIONS

This application is a continuation-in-part of U.S. patent application Ser. No. 14/474,751, titled "Apparatus for Reducing the Appearance and Effects of Scars," filed on Sep. 2, 2014, which claims priority to U.S. Provisional Patent Application No. 61/872,007, titled "Scar Erasing Thimble and Scar Cream," filed on Aug. 30, 2013, which are hereby incorporated by reference.

TECHNICAL FIELD

The present application relates to devices for treating scars, and more particularly, for a textured apparatus that fits on a person's finger and that can be used to reduce the effect and appearance of a scar over a period of time.

BACKGROUND

A scar is a mark that remains on body tissue after it has been damaged. Scars commonly occur after injury to the body tissue, for example as a result of an accident, surgery, disease, or skin condition (e.g., acne). A scar can include tissue that is raised above the surrounding tissue, which can be unaesthetic if the scar is on a human's skin. In addition, scars are often discolored with respect to the surrounding skin. Another problem is that scars on sensitive areas, such as a finger, can be uncomfortable, painful or more susceptible to the same. Painful scars can cause a patient to avoid stimulating the scar area, which can result in the avoidance of use of the scar area (a finger, a hand, etc.) since motion, pressure, and/or tactile stimulation can increase pain in a scar. Furthermore, scars with poor aesthetic appearances can have negative social consequences (e.g., embarrassment, self-consciousness, etc.) for the patient.

It is recognized that rubbing a scar with a frictional tool could reduce the effects of or appearance of the scar in the long term. However, many existing systems for doing this are cumbersome, bulky, heavy, expensive and/or simply inconvenient to use, leaving persons with scars with few options to conveniently and inexpensively treat their scar tissue. In addition, many existing systems require a medical practitioner, such as an occupational or physical therapist, to administer treatment in a formal medical setting (e.g., an office, hospital, etc.), which is less convenient and more expensive for the patient. In addition, scars can be painful, and it has been shown that scar desensitization and mechanical stimulation promote healing and decreased pain levels.

SUMMARY

The present disclosure is directed to a device or a system including a device or devices that treat scars on the skin. The present devices and systems overcome many of the shortcomings of existing devices and systems for treating scars. In an aspect, the present device can improve fingertip hypersensitivity for isolated finger injuries. It can also be used to treat scars anywhere on the body. The embodiments described include convenient and effective form factors such as in the form of a wearable thimble with a textured outer surface that fits over one or more fingers that can apply the thimble to an affected area (scar). For some users the present device could aid in improving (reducing) the size of a scar, improving its appearance, reducing the pain from the scar, and improving edema, swelling as well as sensitivity of certain scars.

An aspect of the invention is directed to an apparatus for treating skin, the apparatus comprising: a substantially cylindrically shaped body having an axial length and a width and having a wall of a finite thickness, and defining a cylindrical cavity suited to receive a finger, said wall having an interior surface defined by said cavity, as well as an exterior surface; said body further having a first end and a second end at opposing ends of said axial length of said body, said first end comprising an aperture to allow a finger to pass through said aperture and into the cavity along said axial length, and the interior surface of the second end conforms to a tip of a finger; said body additionally comprising at least one side opening in a side of said wall; and a textured region defined on at least a portion of the exterior surface of the body, the textured region comprising raised features extending from the exterior surface of the body, the raised features having an elongated shape, wherein a first group of the raised features is oriented in a first direction and a second group of the raised features is oriented in a second direction, the second direction orthogonal to the first direction, wherein the body comprises a compound material that includes a range of about 1% by weight to about 15% by weight of a therapeutic material that treats a dermatological condition and a range of about 85% by weight to about 99% by weight of a moldable material.

In one or more embodiments, the compound material is configured to release a portion of the therapeutic material when heated above room temperature. In one or more embodiments, the therapeutic material treats scar tissue. In one or more embodiments, the textured region includes a grid having a first section comprised of the first group of the raised features and a second section comprised of the second group of the raised features, the first section adjacent to the second section. In one or more embodiments, the moldable material comprises silicone.

Another aspect of the invention is directed to a method for manufacturing an apparatus, comprising: mixing a therapeutic material and a moldable material to form a mixed material, the therapeutic material for treating a dermatological condition; molding the mixed material to form a molded structure that comprises: a substantially cylindrically-shaped body having an axial length and a width and having a wall of a finite thickness, and defining a cylindrical cavity suited to receive a finger, said wall having an interior surface defined by said cavity, as well as an exterior surface; and a textured region defined on at least a portion of the exterior surface of the body, the textured region comprising raised features extending from the exterior surface of the body, the raised features having an elongated shape, wherein a first group of the raised features is oriented in a first direction and a second group of the raised features is oriented in a second direction, the second direction orthogonal to the first direction. The method further comprises curing the molded structure to form the apparatus.

In one or more embodiments, the therapeutic material comprises a therapeutic cream that treats scar tissue. In one or more embodiments, the method further comprises mixing a curing agent with the therapeutic material and the moldable material. In one or more embodiments, the curing agent comprises platinum or a peroxide. In one or more embodiments, the molding step includes heating the mixed material to a temperature within a range of about 300° F. to about 350° F. In one or more embodiments, the curing agent comprises platinum or tin. In one or more embodiments, the molding step includes heating the mixed material to a temperature within a range of about 100° F. to about 225° F.

In one or more embodiments, the molding step includes heating the mixed material to a temperature within a range of about 60° F. to about 120° F. and the curing step includes exposing the molded structured to ultraviolet light. In one or more embodiments, the method further comprises mixing the therapeutic material and the moldable material in a static mixer. In one or more embodiments, the method further comprises pumping the therapeutic material and the moldable material into the static mixer. In one or more embodiments, the moldable material comprises silicone. In one or more embodiments, the molding step includes injection molding or compression molding.

Yet another aspect of the invention is directed to a method for manufacturing an apparatus, comprising: mixing a moldable material and a curing agent to form a mixed material; molding the mixed material to form a molded structure that comprises: a substantially cylindrically-shaped body having an axial length and a width and having a wall of a finite thickness, and defining a cylindrical cavity suited to receive a finger, said wall having an interior surface defined by said cavity, as well as an exterior surface; and a textured region defined on at least a portion of the exterior surface of the body, the textured region comprising raised features extending from the exterior surface of the body, the raised features having an elongated shape, wherein a first group of the raised features is oriented in a first direction and a second group of the raised features is oriented in a second direction, the second direction orthogonal to the first direction. The method further comprises curing the molded structure; exposing the molded structure, for a predetermined time, to a therapeutic material that treats a dermatological condition; and absorbing the therapeutic material in the molded structure to form the apparatus.

In one or more embodiments, the therapeutic material comprises a therapeutic cream that treats scar tissue. In one or more embodiments, the moldable material comprises silicone.

INC THE DRAWINGS

DETAILED DESCRIPTION

Figure 1:
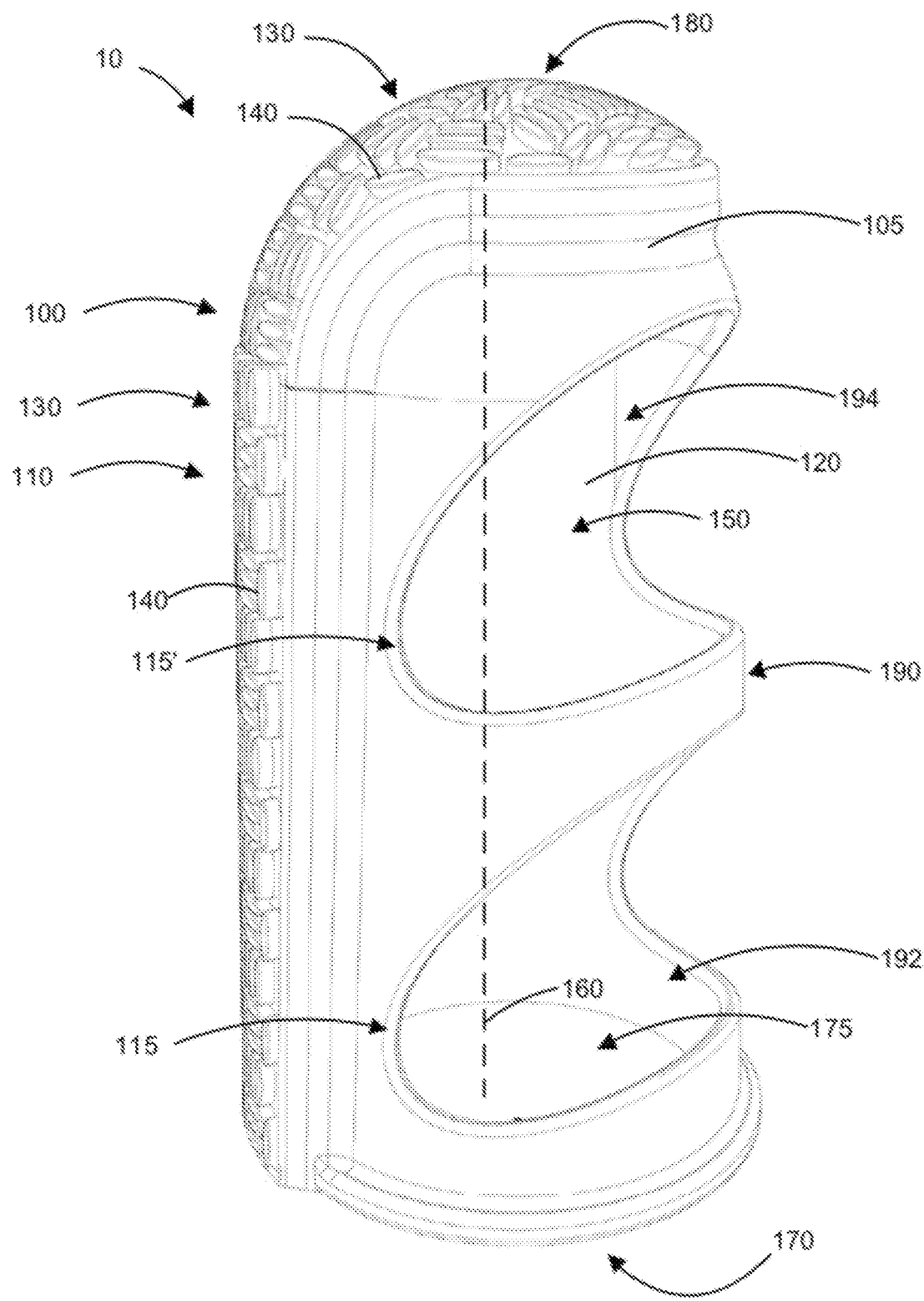
FIG. 1 illustrates a perspective view of a scar treatment thimble according to an exemplary embodiment.

The present disclosure is generally directed to devices and methods for treating localized dermatological conditions in humans and other animals using a wearable device for applying pressure and friction to the affected area. The conditions known to respond to the treatment include scars, burns, keloids, skin blemishes, incisions, lacerations, abrasions, and stretch marks.

A scar therapy kit is also disclosed and can be used as a tool for wound/laceration/incision/abrasion/crush injury recovery by decreasing the appearance and sensitivity of traumatic and/or post-surgical scars throughout the body. For isolated finger injuries, it can also improve fingertip hypersensitivity and minimize scar formation as mentioned above. The kit comprises a scar treatment device or thimble and can comprise a therapeutic cream which could also be applied on and/or within a sheet or a pad. In an aspect, the kit and device allow a person with scar(s) to both actively and passively improve scar recovery.

In general, the wearable device includes a body having an interior surface and an exterior surface. The exterior surface includes features that provide one or more textured regions that a patient can rub against the affected area. The textured regions can have varying coarseness or roughness. The features can include raised bumps, grooves, or other shapes that have a coarseness appropriate for the skin condition and/or the treatment regimen. The textured regions can have features arranged in various patterns, which can have variations within the pattern such as the distance between each feature and adjacent features, the arrangement of the features (e.g., in linear columns and rows or an offset between adjacent columns and/or rows), and/or the hardness or flexibility of the material that creates the features. These variables, described above, can be the same or different across the textured region. The variable geometries can also provide a pathway through which a therapeutic cream can pass through and be evenly or unevenly distributed across the area being treated.

The body has a cavity to receive one or more fingers. A proximal end of the body defines an aperture to allow a finger to penetrate the cavity. The interior surface of the distal end of the body is adapted to conform to the tips of one or more fingers. Thus, a patient can mount the apparatus on a finger by inserting the finger(s) through the proximal end of the body and through the cavity to the distal end of the body.

The cavity can be cylindrical and can have a central axis extending from the proximal end to the distal end of the body. A support member can be disposed on the body to enhance the mechanical strength of the device. The support member can be disposed in an orientation orthogonal to the central axis.

As discussed above, the device has one or more textured regions. For example, a first textured region can have a coarseness appropriate for a first portion of a treatment regimen and a second textured region can have a coarseness appropriate for a second portion of the treatment regimen. The second textured region can have a greater or lower coarseness or roughness than the first textured region. The first and second textured regions can have other variations including the pattern of the features within each textured region, the distance between each feature, the arrangement of the features (e.g., in linear columns and rows or an offset between adjacent columns and/or rows), the distance between each feature and adjacent features, and/or the hardness or flexibility of the material that creates the features. In addition, a therapeutic cream can flow through interstices or channels of the first textured region at a first rate and a therapeutic cream can flow through interstices or channels of the second textured region at a second rate, thereby allowing the cream to flow through the textured regions at the same or different rates.

In addition, a kit with two or more devices is disclosed. A first device, similar to the devices described above, has at least one textured region having a first coarseness appropriate for a first portion of a treatment regimen. A second device, also similar to the devices described above, has at least one textured region having a second coarseness appropriate for a second portion of the treatment regimen. The kit can include additional devices having varying coarseness, which can be used for other portions of the treatment regimen. The kit can also include a cream to be used together or separately from the devices to treat the skin.

The device can be formed by mixing a therapeutic material (e.g., a therapeutic cream), a moldable material, and an optional curing agent to form a first compound material. The first compound material is then molded and heated to form a molded structure, which is then cured. The formed device has the therapeutic material incorporated into its material. When the device is heated or warmed during use (e.g., due to body heat and/or friction caused by rubbing the device against scar tissue), some of the incorporated therapeutic material is released onto the patient's skin on or proximal to the scar tissue (or other dermatological feature).

The device can also be formed by mixing a moldable material and an optional curing agent to form a second compound material. The second compound material is then molded and heated to form a molded structure, which is then cured. After it is cured, the device is exposed to a therapeutic material (e.g., a therapeutic cream) so that at least some of the therapeutic material is absorbed into the device material (e.g., into the cured material or structure). When the device is heated or warmed (e.g., above room temperature) during use (e.g., due to body heat and/or friction caused by rubbing the device against scar tissue), some of the absorbed therapeutic material is released onto the patient's skin on or proximal to the scar tissue (or other dermatological feature).

Unless otherwise indicated, like numbers refer to like features in each drawing. For example reference numbers 110 and 210 refer to like features unless stated otherwise.

FIG. 1 illustrates an exemplary device 10 consistent with the present teachings to treat a localized dermatological condition, e.g., scars, burns, keloids, skin blemishes, and/or stretch marks. The device 10 includes a body 100 having an exterior surface 110 and an interior surface 120. The exterior surface 110 has a textured region 130, which can be defined on the exterior surface 110, comprised of various raised features 140 that extend from the exterior surface 110. As illustrated in FIG. 1, the features 140 have an elongated shape such as oval prisms (i.e., an oval in one plane with a height in an orthogonal plane). In some embodiments, the features 140 can be raised bumps, grooves, ridges, spheres (or semi-spheres, spherical sections, etc.), cubes, parallelepipeds, cones, or other shape that provides an abrasive or textured surface. The features 140 can have a uniform shape (e.g., all oval prisms as illustrated in FIG. 1) or the features 140 can be a combination of two or more shapes, such as a combination of semi-spheres and cubes. Additionally, the features 140 can have a uniform shape but can be oriented in the same direction relative to each other or they can be oriented in two or more directions on the exterior surface 110. Alternatively, the features 140 can be formed from treating the exterior surface 110, such as by sand blasting, scraping, scratching, or other treatment to create a desired coarseness. In addition, the features 140 can be arranged to allow a therapeutic cream (not shown) to flow through the textured region 130, for example in the interstices or channels formed by the features 140. The features 140 can also be used to work the therapeutic cream into the scar tissue (e.g., after the therapeutic cream is placed directly on the scar tissue).

The interior surface 120 of the body 100 is exposed to a cavity 150. The cavity 150 is generally sized to a finger of a patient (not shown). The distal end 180 of the interior surface 120 is shaped to conform to a tip of a finger. The cavity 150 has a central axis 160 that extends from a proximal end 170 to a distal end 180 of the body 100. Although the cavity 150 as illustrated in FIG. 1 is generally cylindrical, the cavity 150 can have other shapes such as a parallelepiped or a polyhedron prism (e.g., an octagon in one plane with a height in an orthogonal plane). In some embodiments, the body 100 is tapered from the proximal end 170 to the distal end 180, such that the body 100 is wider at the proximal end 170 and narrower at the distal end 180.

The body 100 defines an optional first opening 192 between the proximal end 170 of the body 100 and the support member 190. The body 100 further defines an optional second opening 194 between the distal end 180 of the body 100 and the support member 190. As illustrated in FIG. 1, the first opening 192 has approximately the same size and approximately the same shape as the second opening 194. In addition, as illustrated in FIG. 1, the first opening 192 and the second opening 194 are on the same "side" 105 of the body 100 so that they are substantially in alignment with each other along the circumference of the exterior surface 110 of the body 100. The openings 192 and 194 are located approximately 180 degrees from the features 140. However, other relative positions of the openings 192 and 194 and the features 140 are within the scope of this disclosure. For example, the features 140 can be disposed on the exterior surface 110 of the body 100 up to an edge 115 of the exterior surface 110 adjacent the first opening 192 and/or up to an edge 115' of the exterior surface 110 adjacent the second opening 194. The optional first opening 192 and/or the optional second opening 194 can enhance the flexibility of the body 100 by decreasing the mechanical strength of the side 105. In addition, the optional first opening 192 and/or the optional second opening 194 can provide space for the body 100 to flex when a patient bends a finger in the cavity 150 towards the features 140 and away from the side 105. For example, the optional first opening 192 and/or the optional second opening 194 can be arranged to align and/or contour to a shape and/or position of the interphalangeal articulations/joints of the hand, which can enhance flexibility and/or comfort for the patient. In some embodiments, three or more openings are defined in the body 100.

The optional support member 190 is arranged in an orientation orthogonal to the central axis 160 along the circumference of the body 100, although other orientations (e.g., diagonal) are within the scope of the disclosure. The support member 190 can enhance the mechanical strength of the device 10.

The proximal end 170 of the body 100 defines an aperture 175 sized to allow a finger to pass through to the cavity 150. A patient can mount the device 10 on a finger by a fingertip through the aperture 175. The patient can then slide the device 10 down the finger through the cavity 150 so that the fingertip touches the interior surface 120 of the proximal end 180 of the body 100. The patient aligns the openings 192 and 194 with the back (nail side) of the finger so that the pad of the finger faces away from the openings 192 and 194 and towards the features 140. The patient then rubs the features 140 against a scar (or other dermatological condition) for treatment thereof. The textured surface 130 provides an abrasive force that can decrease the scar size and/or decrease the sensitivity of the scar as the scar heals, for example by re-training neuroreceptors connected to the scar tissue to be less sensitive. Also, mechanical stimulation of the scar tissue precipitates formation, reorganization, and maturation of new collagen to further promote favorable scar healing. In addition or in the alternative, a patient can wear the device 10 on a finger that had a recent injury, trauma, or surgery during the healing process (e.g., at night). The device 10 can help retain moisture on the injured finger during healing, which can reduce scar sensitivity (e.g., by re-training neuroreceptors) and scar size.

The device 10 including the body 100 can be formed of a flexible or semi-flexible material such as silicone, fluorosilicone, rubber, thermo-plastic rubber, polyurethane rubber, polyvinyl chloride (PVC), latex, polyisoprene, an elastomer, an elasto-plastic or other plastic or polymeric materials. Examples of silicone material that can be used to form the device 10 include DOW CORNING® QP1 silicone elastomers, such as QP1-30, QP1-50, QP1-60, and/or QP1-70, and/or SILASTIC™ silicone mold-making materials, such as RTV-3481, RTV-3483, RTV-3110 Base, RTV-3112 Base, RTV-3120 Base, RTV-3496 Base, RTV-3497 Base, RTV-3498 Base, RTV-4230-E Base and Curing Agent, RTV-4130-J Base, RTV-4135-L Base, RTV-4136-M Base, RTV-4133-M2 Base and Curing Agent, RTV-4133-M-3 Base, RTV-4131-P1 Base and Curing Agent, RTV-4250-S Base, RTV-4251-S2 Base and Curing Agent, RTV-4232-T2 Base and Curing Agent, RTV-4232-T2 Base/RTV-4232-T2 HD Curing Agent, RTV-4234-T4 Base and Curing Agent, and/or RTV-4260-V Base and Curing Agent. The DOW CORNING® QP1 silicone elastomers and the SILASTIC™ silicone mold-making materials are available from The Dow Chemical Corporation of Midland, Mich. (USA).

The flexible or semi-flexible material can allow the device 10 (e.g., body 100) to conform to the treatment area on a patient. For example, a flexible or semi-flexible material can allow the device 10 (e.g., body 100) to conform to the shape of the skin on a patient's forearm where a scar may be located thereby increasing the surface area of the textured region 130 in contact with the treatment area (e.g., a wound site). In addition, a flexible or semi-flexible material can allow the interior surface 120 of the body 100 to conform to a patient's finger in the cavity 150 when the patient uses the device 10. Also, a flexible or semi-flexible material can be more comfortable to a patient when the device 10 is in contact with a wound site. In addition, a flexible or semi-flexible material can be gentler to a wounded area.

The flexible or semi-flexible material can be combined with a therapeutic material to form a compound material. The therapeutic material can include a therapeutic cream or lotion, such as cream 1440 described below, a moisturizing cream or lotion (e.g., such as cream 1440 discussed below), an emollient, an emulsifier, essential oil, a synthetic or natural pharmacologic composition, and/or another therapeutic material. The therapeutic material can have one or more properties that can treat, heal, soothe, and/or provide another benefit for a dermatological condition or feature, such as scar tissue. [For example, the therapeutic material can be mixed into the flexible or semi-flexible material prior to forming (e.g., by molding such as injection or compression molding) the device 10.

In some embodiments, the compound material includes about 1% to about 20% (by weight or by volume), including about 5%, about 10%, about 15%, and any percentage or percentage range between any two of the foregoing percentages, of therapeutic material and about 80% to about 99% (by weight), including about 85%, about 90%, about 95%, and any percentage or percentage range between any two of the foregoing percentages, of flexible or semi-flexible material. In a specific example, the compound material can include about 1% to about 20% (by weight) of therapeutic cream (e.g., cream 1440) and about 80% to about 99% (by weight) of silicone. In another specific example, the compound material can include about 1% to about 20% (by volume) of therapeutic cream (e.g., cream 1440) and about 80% to about 99% (by volume) of silicone.

In addition, or in the alternative, the therapeutic material can be absorbed into the flexible or semi-flexible material after the device 10 is formed. In an embodiment, the therapeutic material can be mostly aqueous or oil based. In an embodiment, the therapeutic material may be eluted from the device 10 and can be expressed therefrom during use of the device. For example, as the device is applied to a patient, the mechanical agitation, pressure or heating that results can cause the therapeutic material in the device to be expressed onto the affected area being treated. In an embodiment, the therapeutic material can also simply transfer directly onto the patient and treatment area through contact after it is placed onto the working surface of the device.

In some embodiments, the body 100 is formed of a rigid material such as polyethylene, polypropylene, PVC, a thermoplastic material, or other material described herein. The rigid material can enhance the application of a mechanical force applied by a patient to the treatment site using the device 10. In some cases, an electronic sensor 111 can be incorporated into the device, at an interior or exterior surface thereof, or in an internal layer thereof. A sensor can include a pressure sensor, temperature sensor, infra-red sensor, or other sensor that detects the presence or use of the device during treatment. The sensor can be wired to or wirelessly coupled through a wireless communication interface to a processor, which in turn may communicate with a network of other computing machines. The sensor(s) and processor can thus communicate conditions, times, or other data relating to the use of the device and the therapy session. In some embodiments, the electronic circuits coupled to such sensors can inform a physician or clinic or insurance provider if and when the device is used. Specifically, the sensor(s) and processors coupled to the device can be used to report compliance and to encourage use of the device as needed, or to log other data being collected regarding the use of the device. It can also monitor usage time, so that it can signal to the patient to move onto the next phase of treatment or inform a user when a treatment episode is completed (or remains incomplete).

In some embodiments, the interior surface 120 of the body 100 has a "sticky" or frictional material (e.g., a rubber) that prevents a patient's finger from sliding along the interior surface 120 during use, thus allowing the patient's finger to stay engaged with the device 10 during treatment. The "sticky" or frictional material can also prevent the patient's finger from sliding in a direction parallel to the central axis 160 and/or from rotating about the central axis 160 in the cavity 150. For example, making the device 10 from a soft rubber substantially in the shape of a thimble and fitted snugly to securely fit over a finger can aid in the easy and secure application of the device to a patient's digit and keep it there while the device 10 is rubbed onto a scar.

In some embodiments, the body 100 is formed from two or more materials including the materials described above. For example, the body 100 can have an inner "core" made of a first material and an outer layer made of a second material. The inner "core" can be the portion of the body 100 exposed to the interior surface 120. Likewise, the outer layer can be the portion of the body 100 exposed to the exterior surface 110. In this way, the body 100 can be formed of materials having different properties. As an example, the inner "core" can be made out of a rigid material that has a "sticky" or frictional surface (e.g., a rubber) while the outer layer can be made out of a flexible material. An advantage of this approach is that the rigid material of the inner core increases the translation of mechanical force from a patient's finger to the treatment area while the flexible material of the outer layer increases the surface area of the textured region 130 in contact with the treatment site. The body 100 can include additional layers consistent with this disclosure. In another example, the body 100 can be formed out of two more materials in "strips" that run parallel to or perpendicular to the central axis 160, as discussed in more detail below.

The features 140 can be formed out of the same or a different material than the body 100 or a combination of different materials. In some embodiments, the features 140 are formed out of a flexible or semi-flexible material and the body 100 is formed out of a rigid material. In other embodiments, the features 140 are formed out of a rigid material and the body 100 is formed out of a flexible or semi-flexible material. In some embodiments, a first group of features 140 is made of a first material (e.g., a flexible material) and a second group of features 140 is made of a second material (e.g., a semi-flexible material) to allow a patient to select features having properties (e.g., flexibility or softness) appropriate for a treatment regimen. For example, a patient can select a gentler flexible material for a first portion of a treatment regimen (e.g., week 1) and an incrementally more rigid material (e.g., semi-flexible) for a second portion of a treatment regimen (e.g., week 2) and so on. In some embodiments, the features 140 are formed integrally with the body 100 during an injection molding or similar process. In addition, the features 140 can be arranged to allow a therapeutic cream (not shown) to flow through the textured region 130, for example in the interstices or channels formed between the features 140 and the patient's skin. The width of the interstices or channels can vary depending on the material of the features 140. For example, a wide channel (allowing flow of more cream thus increasing the cream's permeability into the skin both in quantity/time and surface area) can be formed when the features 140 are formed out of a rigid material. In contrast, a narrow channel (allowing for flow of less cream thus decreasing the cream's permeability into the skin both in quantity/time and surface area) can be formed when the features 140 are formed out of a flexible material.

Figure 2:
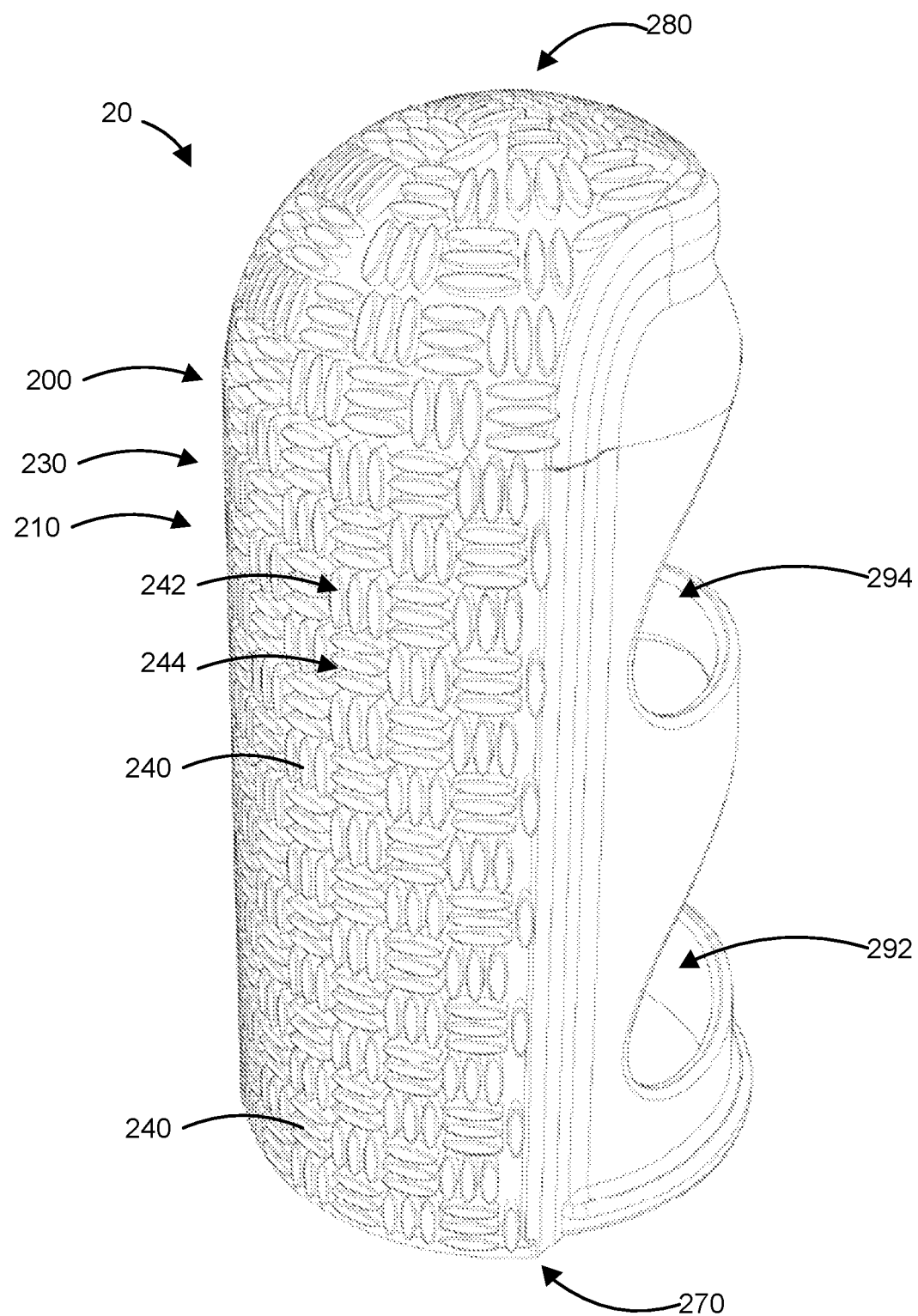
FIG. 2 illustrates another perspective view of a scar treatment thimble according to an exemplary embodiment.

FIG. 2 illustrates a device 20 like the one shown in FIG. 1 but from a different perspective. The device 20 includes a textured region 230 on an exterior surface 210 of a body 200. The textured region 230 includes a plurality of features 240 having the same shape but arranged in a grid pattern based on orientation of the features 240. The grid includes a first group 242 of features 240 arranged in a first orientation and a second and a second group 244 of features 240 arranged in a second orientation. As illustrated in FIG. 2, the features 240 have an elongated shape (e.g., are oval prisms) though it is to be noted that this disclosure is not limited to a particular shape and that oval prisms are only provided as an example. The first group 242 of features 240 is oriented so that the elongated portion of the oval extends from a proximal end 270 to a distal end 280 of the body 200. The second group 244 of features 240 is oriented so that the elongated portion of the oval extends in a direction orthogonal to the elongated portion of ovals in the first group 242 of features 240. The relative orientation of the features 240 can affect the width and/or shape of the interstices or channels formed between the features 240 and the patient's skin. The relative orientation of the features 240 can also affect the coarseness of the textured region 230.

The first group 242 of features 240 is adjacent to the second group 244 of features 240. As illustrated, the first group 242 and the second group 244 are arranged on the exterior surface 210 in a repeating, grid-like pattern to form the textured region 230. It should be noted that other orientations of the features 240 and/or groups of features 240 are included within this disclosure. For example, the first group 242 can include a set of three features 240 where the outer features 240 have one orientation and the inner feature 240 has a different orientation. Likewise, the features 240 in the first group 242 can each have a different orientation. The first group can have additional or fewer features 240 than the three features 240 illustrated in FIG. 2, such as four features 240 or two features 240. Similar variations can be made with respect to the second group 244 of features 240. In some embodiments, the features 240 are divided into three or more groups and arranged in various orientations and/or shapes within each group as described above.

Figure 3:
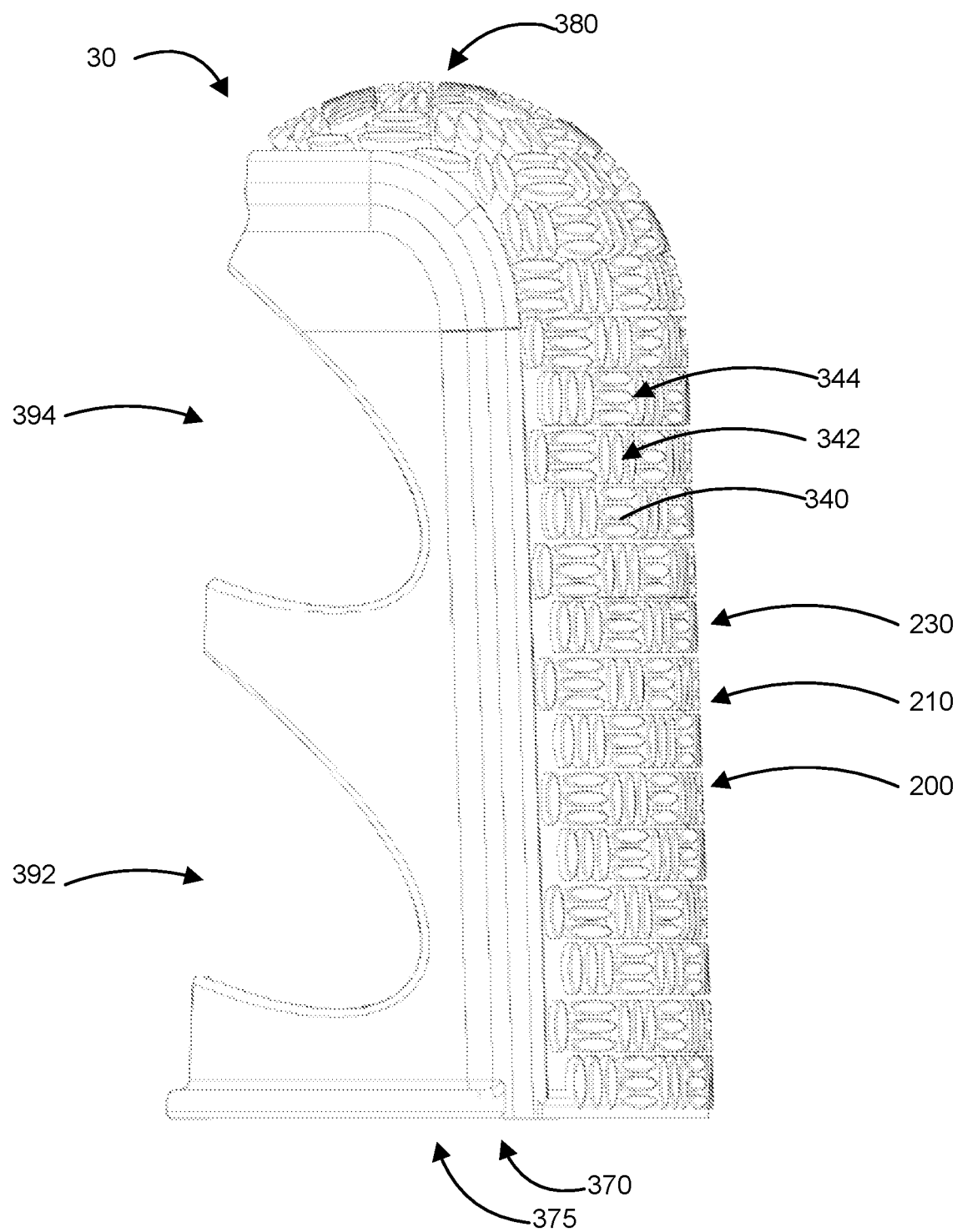
FIG. 3 illustrates a side view of a scar treatment thimble according to an exemplary embodiment.

FIG. 3 illustrates another exemplary perspective of a device 30 similar to the devices 10 and 20 illustrated in FIGS. 1 and 2, respectively, where like numbers refer to like features in other drawings.

Figure 4:
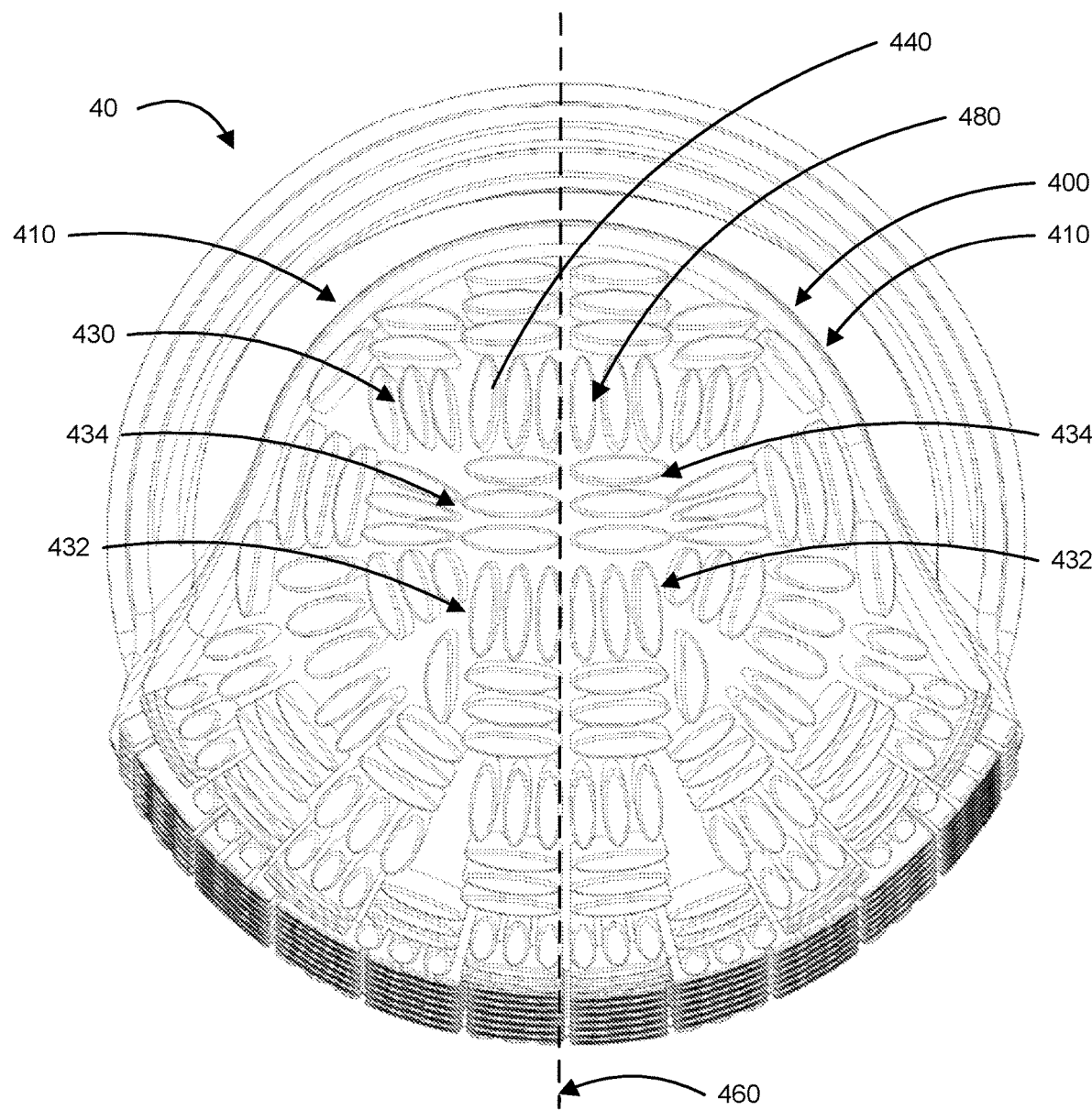
FIG. 4 illustrates a top view of a scar treatment thimble according to an exemplary embodiment.

FIG. 4 illustrates a top view of a device 40 similar to the devices 10, 20, and 30 illustrated in FIGS. 1, 2, and 3, respectively. As shown in FIG. 3, textured region 430 optionally extends to the distal portion 480 of the body 400. The textured region 430 of exterior surface 410 includes a first group 432 of features 440 and a second group 434 of features 440. The first group 432 of features 440 is disposed laterally from another first group 432 of features 440 with respect to an axis 460. Above and below the first group 432 of features 440, with respect to the axis 460, are a pair of the second group 434 of features 440. Additional arrangements of the first group 432 and the second 434 of features 440 are contemplated within this disclosure, as discussed above, including additional groups of features 440 and a different number of features 440 in each group. The features 440 can be arranged to form a channel within the features 440 and/or between the features 440 and the treatment area to allow a cream to flow therethrough.

Figure 5:
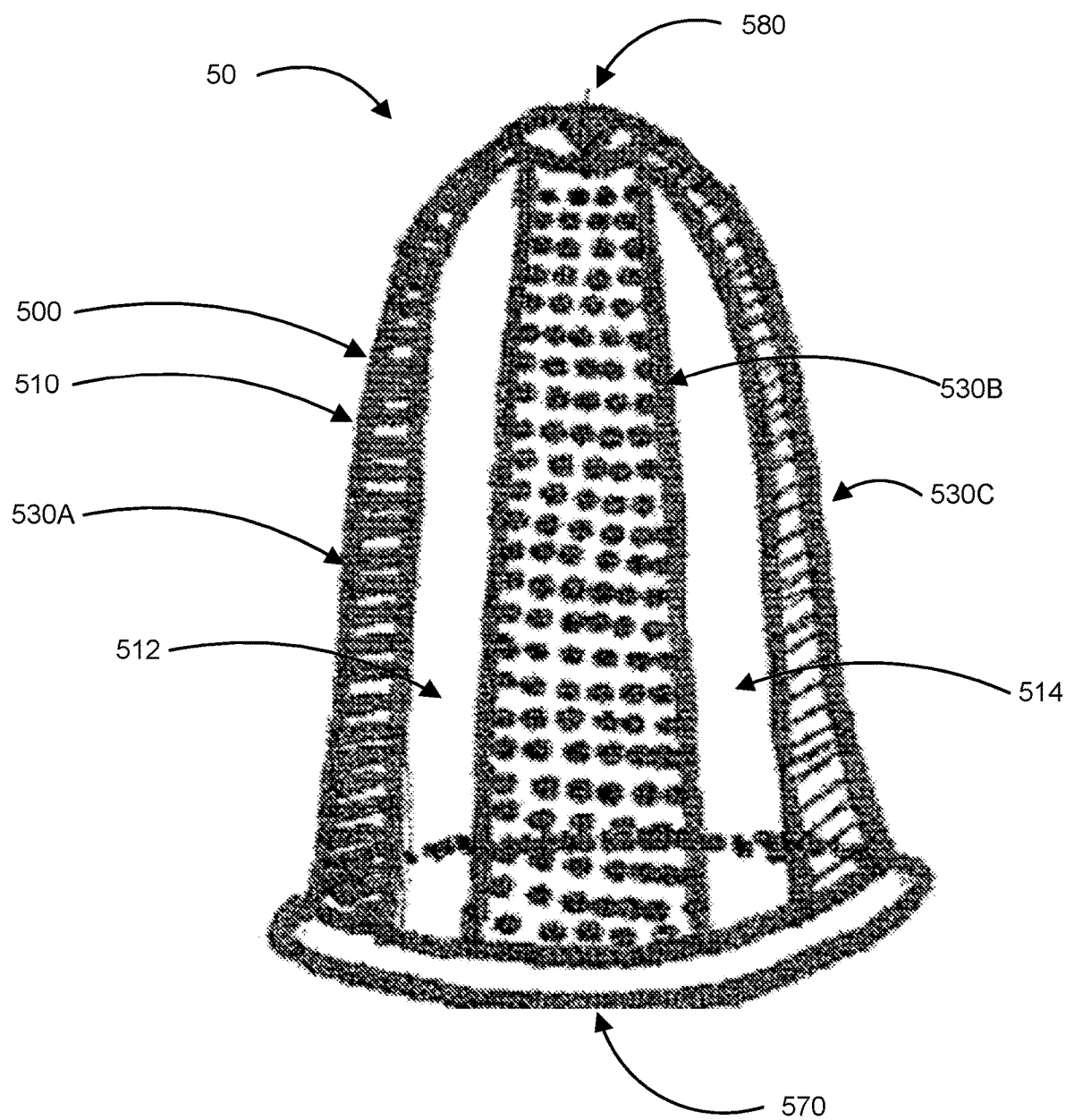
FIG. 5 illustrates a multi-coarseness scar treatment thimble device according to an exemplary embodiment.

FIG. 5 illustrates another embodiment of a device 50. The device 50 has a generally cylindrical body 500 having an exterior surface 510 and an interior surface (not shown). Textured regions 530A, 530B, and 530C are on the exterior surface 510. The textured regions 530A, 530B, and 530C extend vertically from a proximal end 570 to a distal end 580 of the body 500. The textured regions 530A, 530B, and 530C are arranged laterally across a circumference of the exterior surface 510 of the body 500. Optionally, a plain or non-textured region 512 is disposed between textured regions 530A and 530B. Another optional plain or non-textured region 514 is disposed between textured regions 530B and 530C. In some embodiments, the textured region 530A is adjacent to the textured region 530B without the optional plain or non-textured region 512 between the textured regions 530A and 530B. Likewise, the textured region 530B can be adjacent to the textured region 530C without the optional plain or non-textured texture 514 between the textured regions 530B and 530C. The textured regions 530A, 530B, and 530C can be made out of the same material (e.g., with different sizes or shapes of features 540 (not shown)) or they can be made out of different materials (e.g., materials with different flexibilities or softness as discussed above).

The textured regions 530A, 530B, and 530C can have the same coarseness or they can each have a different coarseness. For example, textured region 530A can have a first coarseness, textured region 530B can have a second coarseness, and textured region 530C can have a third coarseness, and so on. In some embodiments, textured region 530C is coarser than textured region 530B, and textured region 530B is coarser than textured region 530A. In this way, a patient can use the device 50 for a treatment plan or regimen having three portions (e.g., a three-week treatment regimen, a six-week treatment regimen, etc.). In the first treatment portion (e.g., the first 1-2 weeks), a patient can use textured region 530A to treat a scar such as by rubbing textured region 530A against the scar. Textured region 530A can have a fine or non-rough coarseness to gently treat the scar as it first starts to heal and/or while the scar has increased sensitivity. In the second treatment portion (e.g., the second 1-2 weeks), the patient can use textured region 530B to treat the scar such as by rubbing textured region 530B against the scar. Textured region 530B can have an incrementally rougher or greater coarseness than textured region 530A, which allows the patient to apply a greater abrasive force to the scar (e.g., since the wound has healed more and is less sensitive since the first treatment portion) by using textured region 530B instead of textured region 530A. In the third portion (e.g., the third 1-2 weeks), the patient can use textured region 530C to treat the scar, such as by rubbing textured region 530C against the scar. Textured region 530C can have an incrementally rougher or greater coarseness than textured region 530B, which allows the patient to apply a greater abrasive force to the scar (e.g., since the wound has healed more and is less sensitive than it was in the second treatment portion) by using textured region 530C instead of textured region 530B. Greater or fewer textured regions 530N (not shown) can be included in the device 50 for additional or fewer treatment portions, or they can be used in combination during the same treatment portion (e.g., textured regions 530A and 530B are both used during week 1 of treatment). A treatment regimen such as the one described above can decrease the scar size and/or decrease the sensitivity of the scar tissue.

Alternatively, treatment portions 530A, 530B, and 530C can be disposed in bands along the circumference of the exterior surface 510 of the body 500. For example, textured region 530A can be in a first band adjacent to the proximal end 570 of the body 500. Textured region 530B can be in a second band adjacent to the first band, where the second band is located transversely from the first band in the direction of the distal end 580 of the body 500. Similarly, textured region 530C can be in a third band adjacent to the second band, where the third band is located transversely from the second band in the direction of the distal end 580 of the body 500. The bands can be made out of the same material or different materials as described above.

Figure 6:
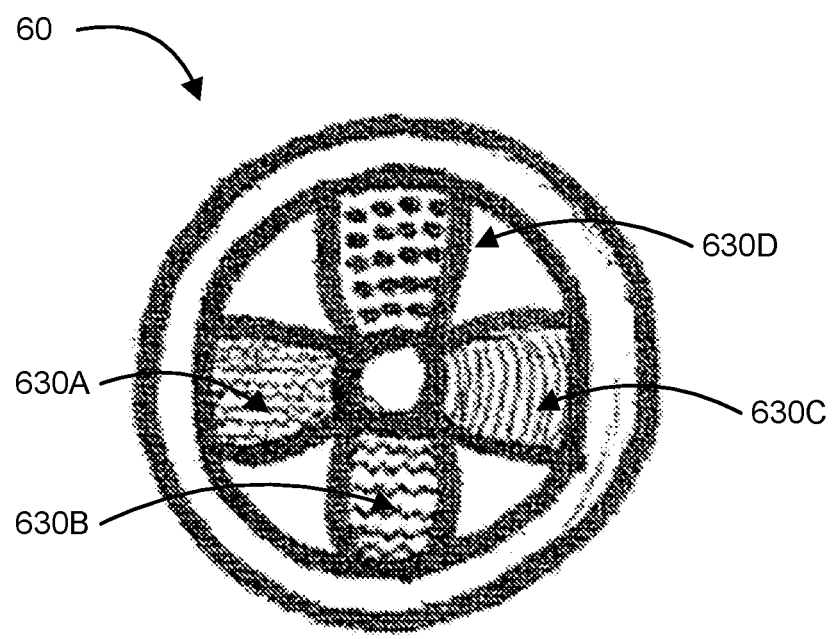
FIG. 6 illustrates a top view of a multi-coarseness scar treatment thimble device according to an exemplary embodiment.

FIG. 6 illustrates a bottom view of a device 60 similar to the device 50 illustrated in FIG. 5. The device 60 includes a body 600 having an exterior surface (not shown) with textured regions 630A, 630B, 630C, and 630D. The textured regions 630A, 630B, 630C, and 630D can each have a different roughness, the same roughness, or combination thereof (e.g., two textured regions have the same roughness and two textured regions a different roughness). In addition, the textured regions 630A, 630B, 630C, and 630D can be made out of the same material or different material as discussed above.

Figure 7:
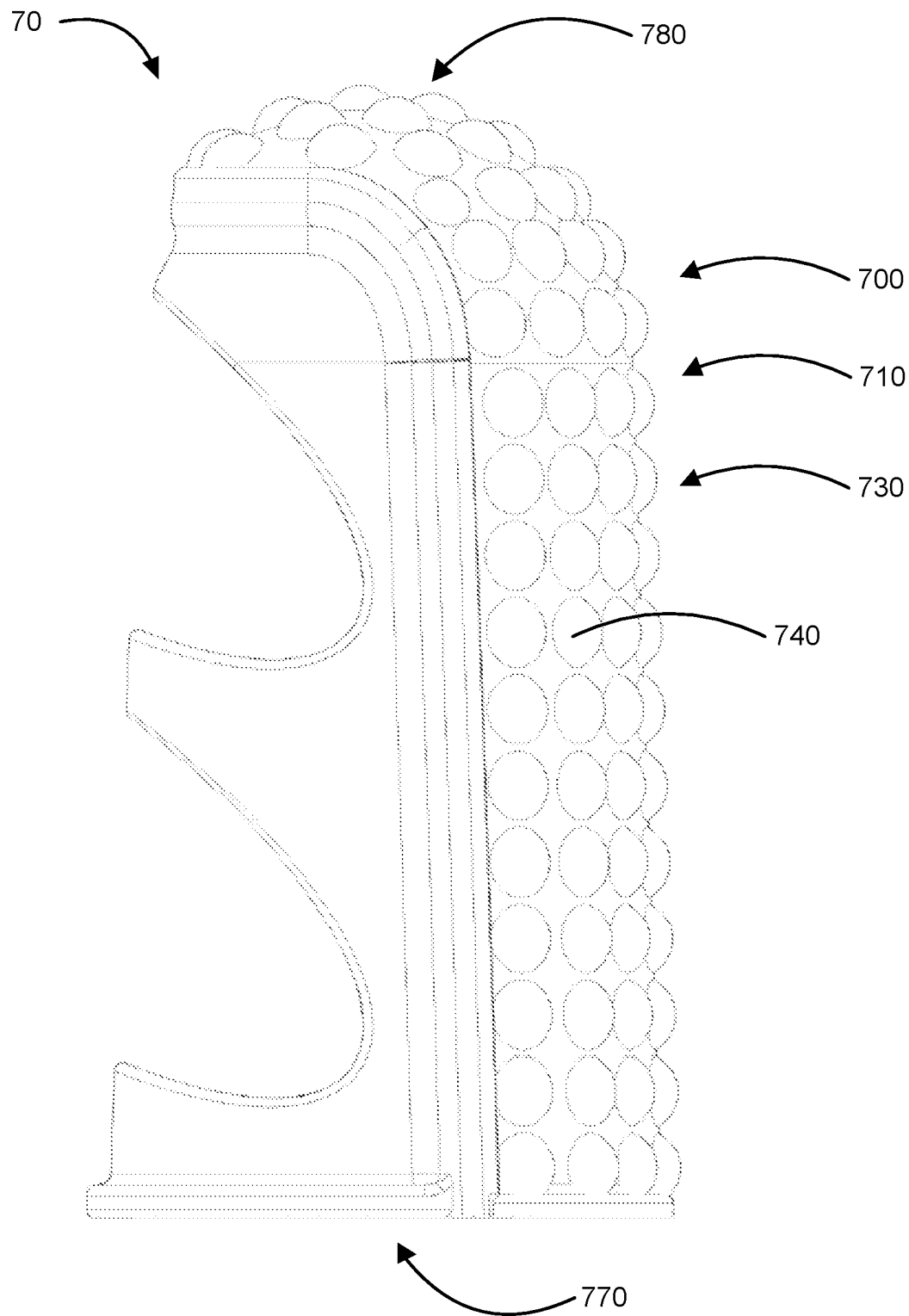
FIG. 7 illustrates a side view of another exemplary scar treatment thimble device.

FIG. 7 illustrates a perspective view of a device 70 according to another embodiment of the invention. The device 70 has a textured region 730 on an exterior surface 710 of a body 700, extending from proximal end 770 to distal end 780. The textured region 730 is comprised of semi-spherical features 740 having a given coarseness or roughness. The coarseness of the textured region 730 can be modified by adjusting the radius of the semi-spherical features 740, and/or by varying the distance between adjacent features 740 and/or the material of the features 740.

Figure 8:
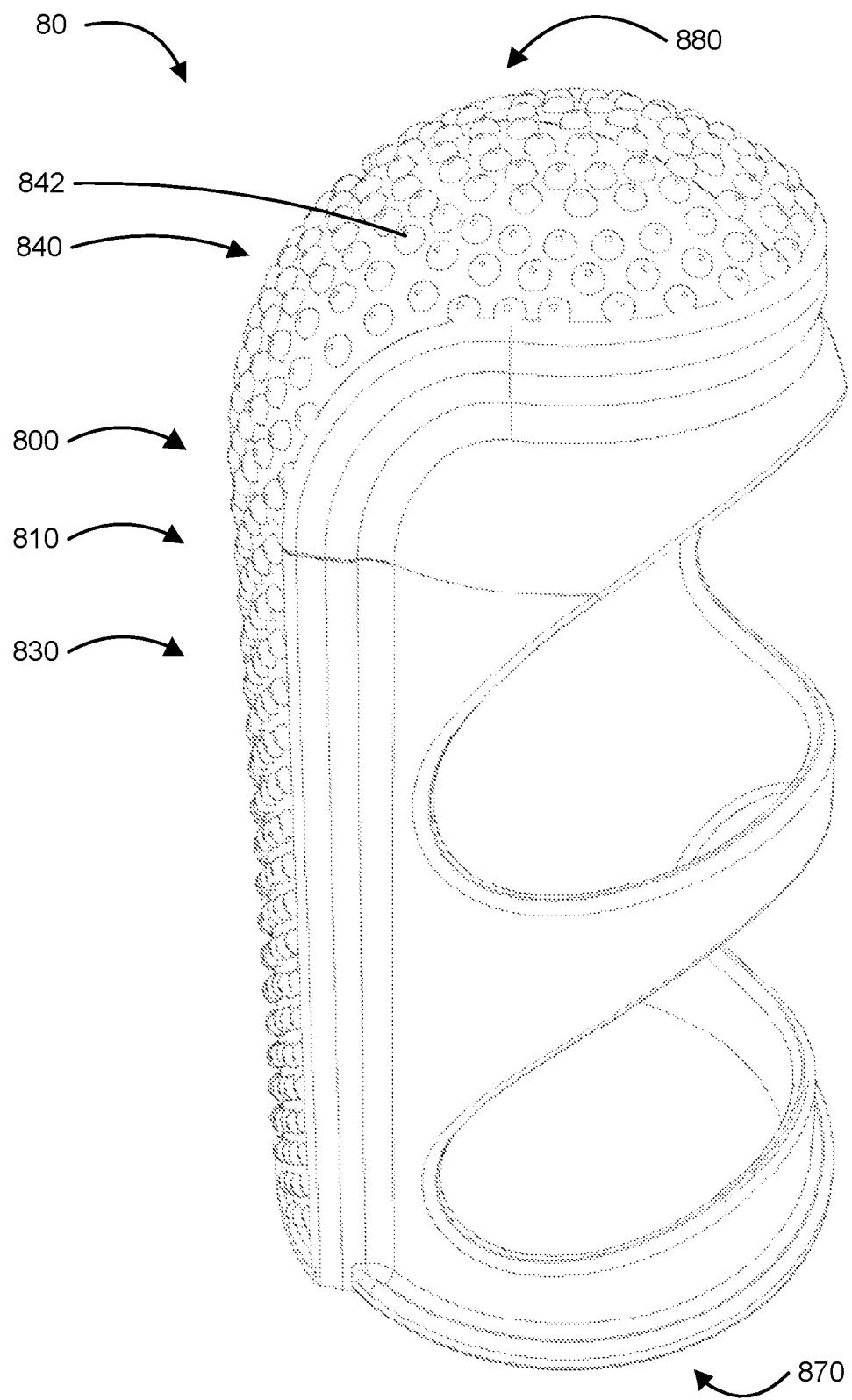
FIG. 8 illustrates a perspective view of another exemplary scar treatment thimble device.

FIG. 8 illustrates a perspective view of another embodiment of the invention. Device 80 has a textured region 830 on an exterior surface 810 of a body 800, extending from proximal end 870 to distal end 880. The textured region 830 is comprised of relatively small, semi-spherical features 840 having a projection 842 extending from the feature 840 away from the body 800. The coarseness of the textured region 830 can be modified by adjusting the radius of the semi-spherical features 840, the height or thickness of the projection 842, and/or by varying the distance between adjacent features 840 and/or the material of the features 840.

Figure 9:
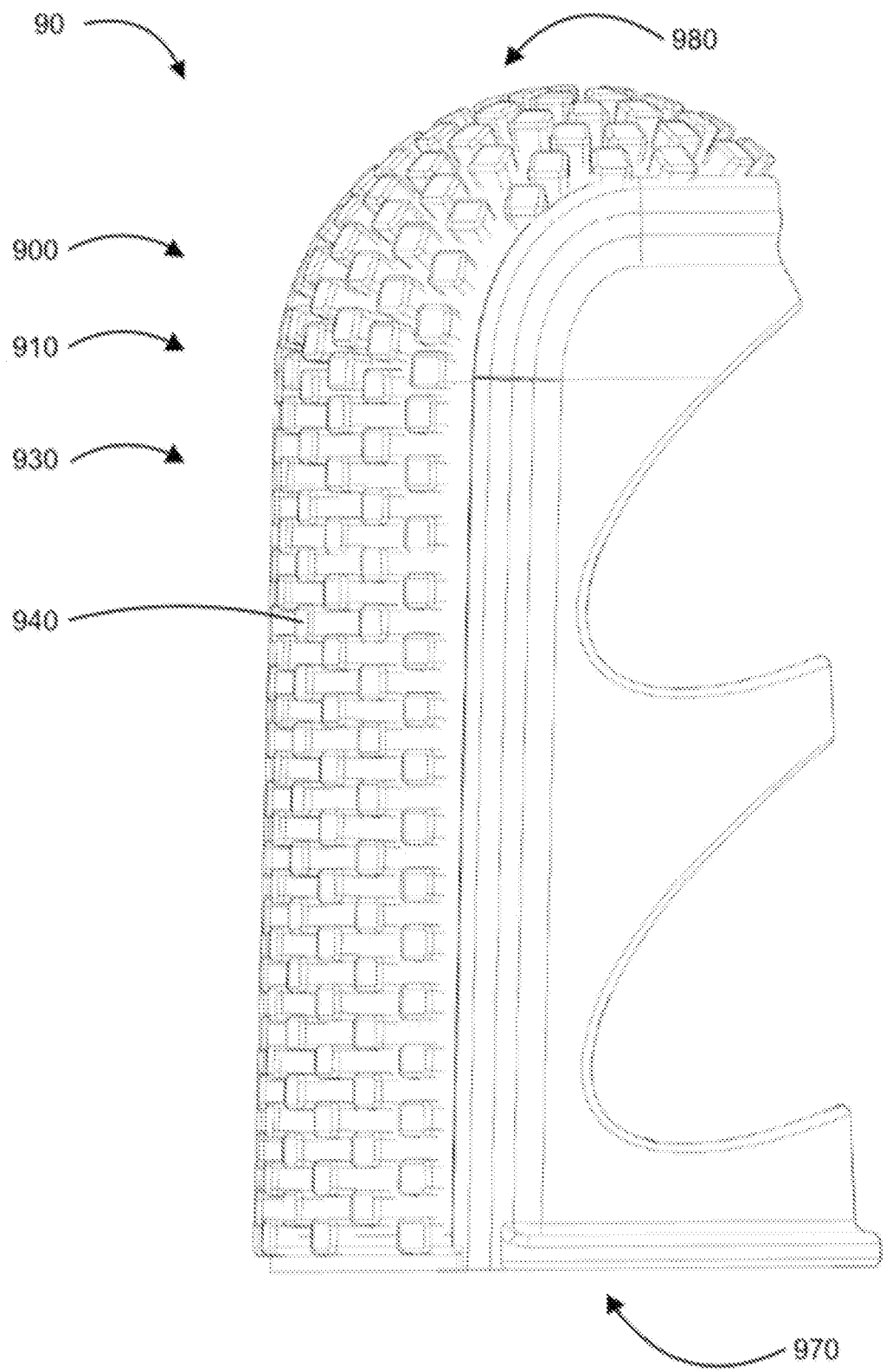
FIG. 9 illustrates a side view of another exemplary scar treatment thimble device.

FIG. 9 illustrates a side view of another embodiment of the invention. Device 90 has a textured region 930 on an exterior surface 910 of a body 900, extending from proximal end 970 to distal end 980. The textured region 930 is comprised of generally flat features 940, such as rectangular prisms. The coarseness of the textured region 930 can be modified by adjusting the size of the features (length, width, and/or height), and/or by varying the distance between adjacent features 940.

Figure 10:
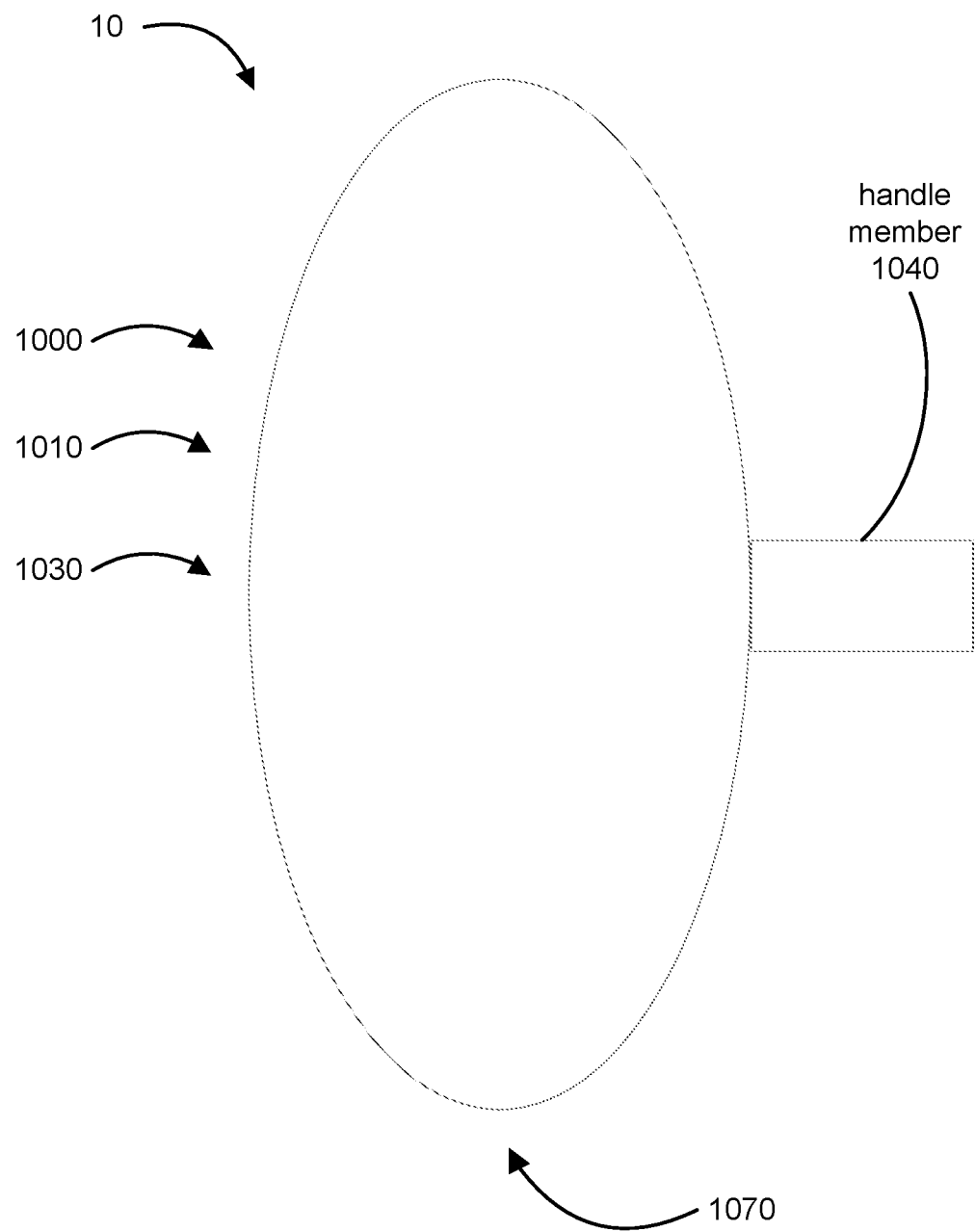
FIG. 10 illustrates a side view of another exemplary scar treatment thimble device.

FIG. 10 illustrates a side view of another embodiment of the invention. Device 10 has a textured region 1030 on an exterior surface 1010 of a body 1000. As illustrated, the body 1000 is optionally closed and does not include a cavity for a finger. In some embodiments, the body 1000 includes a cavity (not shown) for receiving a finger, similar to the cavities described above (e.g., in FIG. 1). Likewise, the body 1000 can include an aperture (not shown) in a proximal portion 1070 of the body 1000, similar to the apertures described above (e.g. in FIG. 1). The body 1000 has a handle member 1040 that allows a patient to hold the device 10 and to rub the device against a scar or other treatment area. The patient can hold the device 10 by the handle member 1040 alone or can use the handle member 1040 while the device 10 is mounted on a finger. The handle member 1040 can be a block, a knob, or other shape that allows a person to hold the device 10.

Figure 11A:
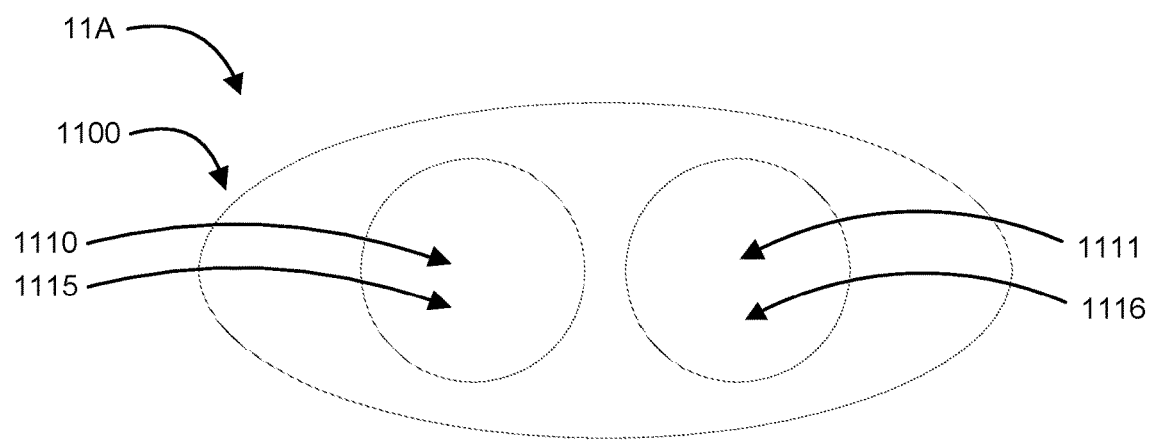
FIGS. 11A and 11B illustrate a bottom view of exemplary scar treatment thimble devices.
Figure 11B:
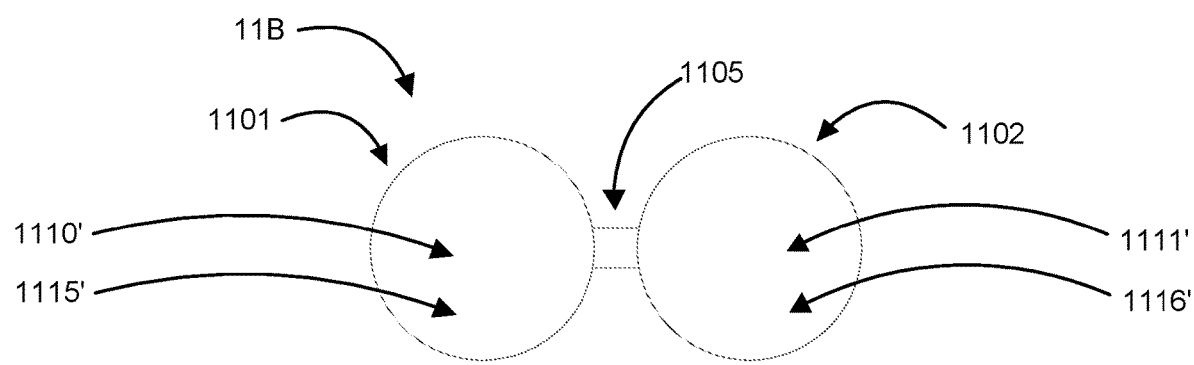

FIGS. 11A and 11B illustrate a bottom view of exemplary scar treatment thimble devices 11A and 11B, respectively. Device 11A has a body 1100 that defines a first aperture 1110 for receiving a first finger and a second aperture 1111 for receiving a second finger. The body 1100 has at least one textured region (not shown) with features that provide a coarseness as described above. In some embodiments, the body 1100 has two, three, four, or more textured regions (not shown). The textured regions and/or features can be made out of the same or different materials as other textured regions on the body 1100. In addition, the textured region(s) can correspond to a portion of a treatment regimen for treating a scar or other dermatological feature. A person can wear the device 11A by inserting a first finger though the first aperture 1110 and into a first cavity 1115 in the body 1100, and by inserting a second finger through the second aperture 1111 and into a second cavity 1116. Distal portions (not shown) of the first cavity 1115 and/or the second cavity 1116 can be shaped to conform to a fingertip, as described in other embodiments. In some embodiments, the body 1100 defines three or more apertures and respective cavities for receiving three or more fingers.

With respect to FIG. 11B, the device 11B includes a first body 1101 and a second body 1102 connected by a bridge 1105. The first body 1101 defines a first aperture 1110' that connects to a first cavity 1115'. The second body 1102 defines a second aperture 1111' that connects to a second cavity 1116'. Each body 1101, 1102 has a textured region (not shown) with features (not shown) that provide a coarseness as described above. In some embodiments, one or both bodies 1101, 1102 has multiple (e.g., two, three, four, or more) textured regions. Each textured region can be made out of the same material or a different material. In some embodiments, the textured region(s) correspond to a portion of a treatment regimen for treating a scar or other dermatological feature.

Figure 12:
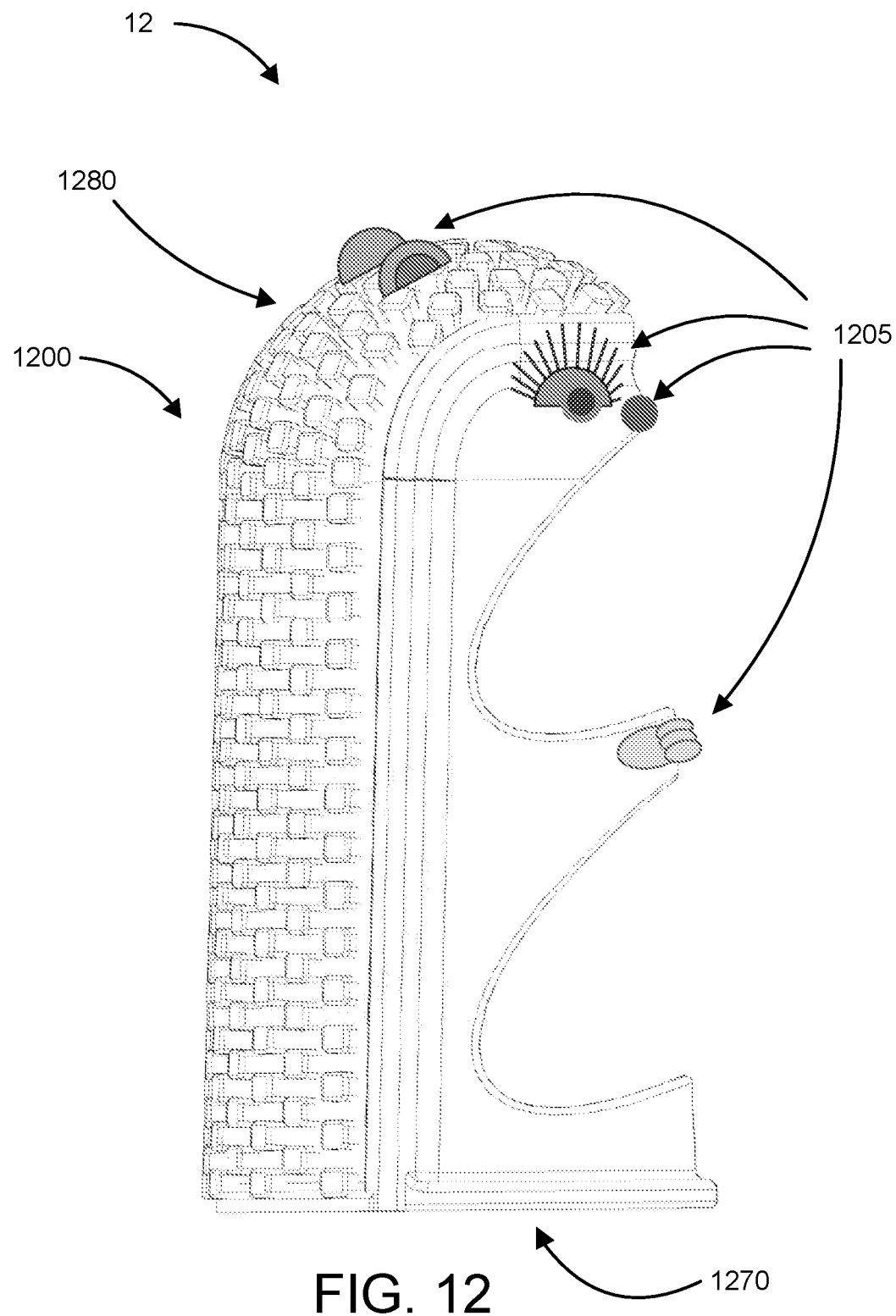
FIG. 12 illustrates a side view of another exemplary scar treatment thimble device.

FIG. 12 illustrates a side view of another embodiment of the invention. As illustrated in FIG. 12, a device 12 includes animal or caricature features 1205 (e.g., nose, eyes, mouth, ears, paws, etc.) on a body 1200 having a proximal end 1270 and a distal end 1280. The animal or caricature features 1205 can be amusing or less intimidating for a child when using the device 12. In some embodiments, a cartoon character or a superhero likeness is disposed on the device 12. In some embodiments, the body 1200 itself is formed to resemble an animal shape, for example with a head at distal end 1280. In some embodiments, the device 12 can have a fun color (pink, yellow, blue, etc.) or pattern (polka dot, stripe, plaid, etc.) that can be appropriate for a child. The device 12 can have various textured regions, features, and materials as described herein.

Figure 13:
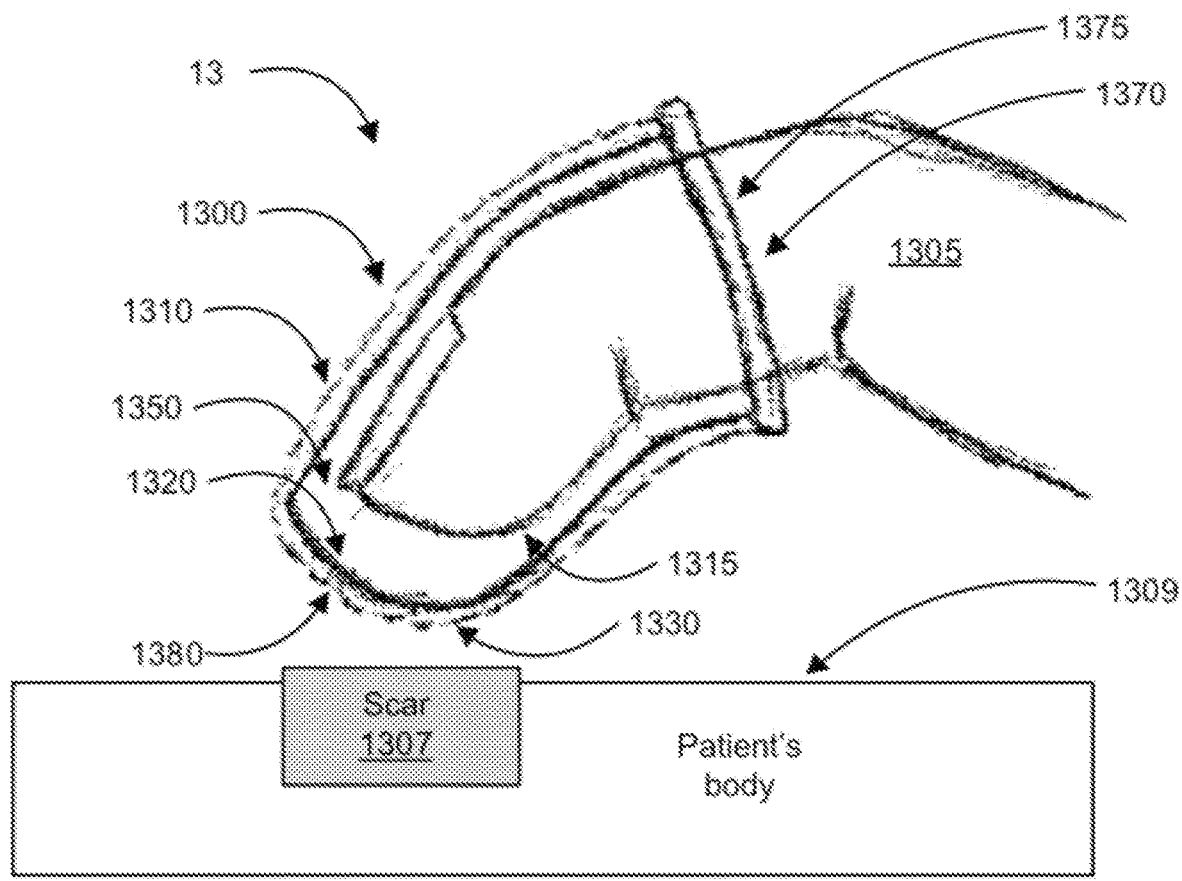
FIG. 13 illustrates application of a scar treatment thimble apparatus to a scar.

FIG. 13 illustrates a non-detailed view of a device 13 on a finger 1305 of a patient. The patient mounts the device 13 on the finger 1305 by inserting a fingertip 1315 through an aperture 1375 in a proximal end 1370 of a body 1300. The patient then slides the device 13 down the finger 1305 such that fingertip 1315 passes through a cavity 1350 and touches an interior surface 1320 of a distal end 1380 of the body 1300. As illustrated, the interior surface 1320 of the distal end 1380 of the body 1300 conforms to the fingertip 1315. For treatment, the patient rubs a textured region 1330 on an exterior surface 1310 of the body 1300 against a scar 1307 (or other dermatological condition) on a patient's body 1309. In some embodiments, the device 13 is adapted to be worn on two or more fingers 1305.

Figure 14:
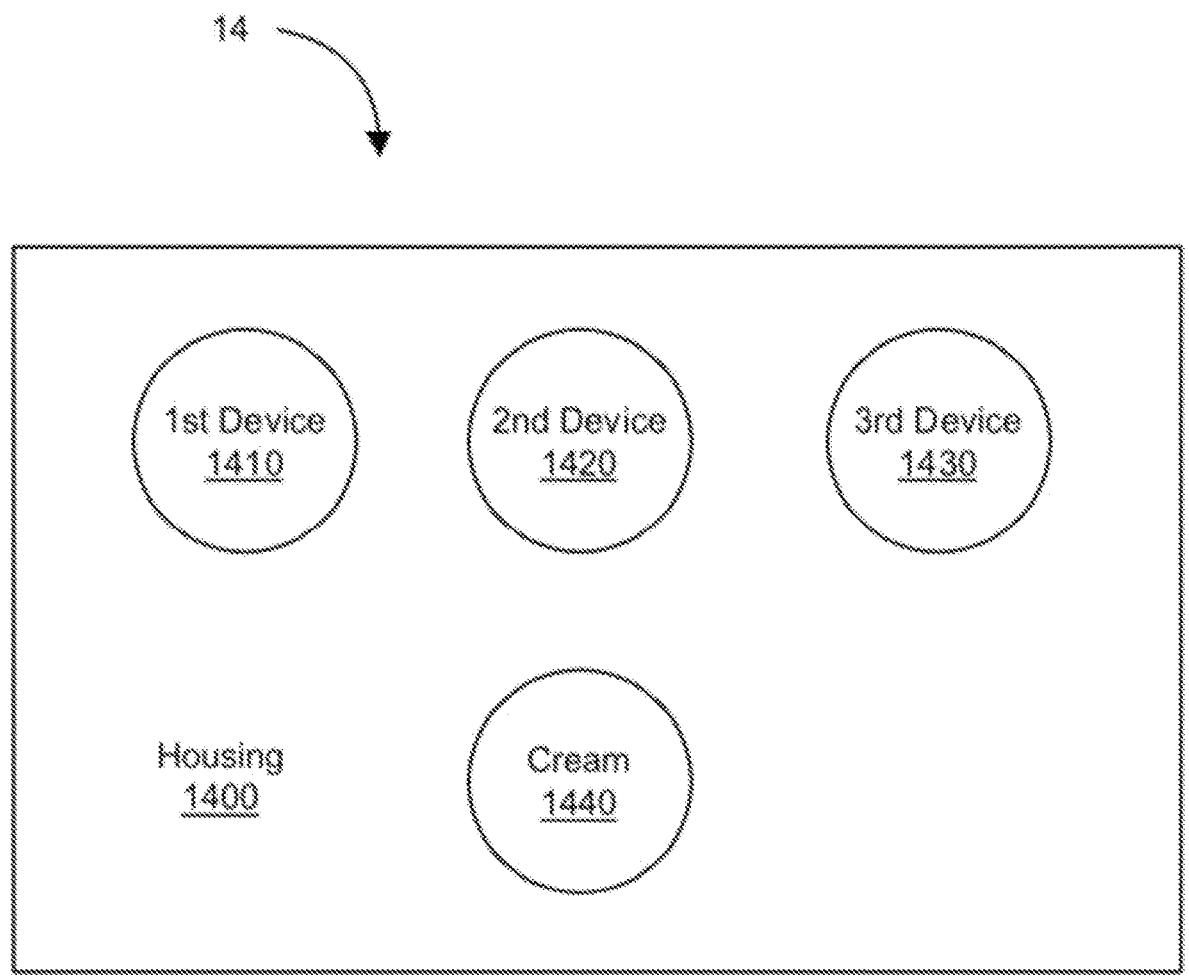
FIG. 14 illustrates a configuration of scar treatment devices in a kit for personal scar care.

FIG. 14 illustrates a kit 14 for treating a dermatological condition. The kit 14 includes a housing 1400 containing a first device 1410, a second device 1420, and a third device 1430. The devices 1410, 1420, and 1430 can be substantially similar to one or more of the devices described above. For example, the devices 1410, 1420, and 1430 can be substantially similar to the device 10. The devices 1410, 1420, and 1430 can have textured regions (not shown) having the same or different coarseness. For example, device 1410 can have a textured region (not shown) with a first coarseness, device 1420 can have a textured region (not shown) with a second coarseness, and device 1430 can have a textured region (not shown) with a third coarseness. In some embodiments, the devices 1410, 1420, and 1430 have textured regions that are progressively coarser. For example, device 1410 can have a textured region that is relatively fine or non-coarse; device 1420 can have a textured region that his incrementally more coarse or rough than that of device 1410; and device 1430 can have a textured region that his incrementally more coarse or rough than that of device 1420. In other words, device 1410 can be the least coarse, device 1430 can be the most coarse, and device 1420 can have a "middle" coarseness. Each device 1410, 1420, and 1430 can be made out of the same or different materials as described above.

Similarly, each device 1410, 1420, and 1430 has the same or different feature shape (not shown). For example, device 1410 can have features (not shown) that are oval prisms (e.g., as illustrated in FIG. 1) while device 1420 can have features (not shown) that are semi-spheres (e.g., as illustrated in FIG. 7). Device 1430 can have features (not shown) that are oval prisms, semi-spheres, ridges, another shape or a combination thereof. The features of each device 1410, 1420, and 1430 can be arranged in a pattern, randomly, or a combination thereof.

The texture/coarseness of the devices 1410, 1420, and 1430 can correspond to a step or portion of a treatment regimen. For example, a patient can use device 1410 for a first portion of a treatment regimen (e.g., first 1-2 weeks) followed by device 1420 for a second portion of a treatment regimen (e.g., second 1-2 weeks) and device 1430 for a third portion of a treatment regimen (e.g., third 1-2 weeks). Additional devices can be provided for additional portions of a treatment regimen. The devices 1410, 1420, and 1430 can have writing, coloring, or another indicator to connect the appropriate device with the appropriate portion of the treatment regimen. For example, each device 1410, 1420, and 1430 can have a number inscribed on its surface to designate the week number to use the appropriate device 1410, 1420, and 1430 (e.g., device 1410 has a "1" inscribed on its surface, etc.). In some embodiments, one or more of devices 1410, 1420, and 1430 has a textured surface having two or more regions with a different coarseness (e.g., similar to device 50 in FIG. 5). In some embodiments, one or more of devices 1410, 1420, and 1430 has a handle and/or does not include cavity or aperture for receiving a finger. In some embodiments, one or more of devices 1410, 1420, and 1430 has a cavity and aperture for receiving two or more fingers.

In some embodiments, the kit 14 includes a cream 1440 that can be used to treat the dermatological condition together or in combination with the devices 1410, 1420, and 1430. The cream 1440 can include one, some, or all of the ingredients in Table 1. It is noted that the weight percentages provided in Table 1 are examples and are not intended to be exhaustive. For example, the cream 1440 can include plus or minus 1%, 2.5%, 5%, 10%, or 15% of the weight percentage of any ingredient listed in Table 1. The cream 1440 can have a pH of about 5.9 (at 25° C.) plus or minus 1%, 2.5%, 5%, 10%, or 15% and it can have a viscosity of about 200,000 cps plus or minus 1%, 2.5%, 5%, 10%, or 15%.

TABLE 1

| Ingredient | Weight Percent | Function |
| --- | --- | --- |
| Deionized water | 57.30 | Vehicle |
| Glycerin | 5.00 | Humectant |
| Propanediol | 2.00 | Solvent moisturizer |
| SabiWhite ™ (tetrahydrocurcumin 95%) (Sabinsa Corporation) | 0.20 | Skin lightener, antioxidant |
| Aloe barbedensis | 2.00 | Anti-inflammatory |
| Carbopol ® Ultrez 10 (carbomer) (Lubrizol Corporation) | 0.80 | Rheology, viscosity |
| Vital ET ™ (disodiumLauriminodipropionate tocopheryl phosphates) (Ashland Inc.) | 2.50 | VE phosphate non-steroidal anti-inflammatory, source of Vitamin E |
| Allantoin | 0.50 | Stimulates new tissue growth, wound healing |
| Muira puama (*ptychopetalum olacoides* bark/root extract (and) glycerin (and) water) | 0.50 | Increase blood flow, antiseptic, antibacterial |
| Cutina ® GMS V (glyceryl stearate) (BASF Corporation) | 1.00 | Emulsifier |
| Phenoxyl T (cetearyl alcohol (and) ceteareth-20) | 2.00 | Emulsifier |
| Alpha-bisabolol | 0.20 | Non-steroidal anti-inflammatory |
| Cocoa butter (theobroma cacao seed butter) | 2.00 | Reduces degeneration of skin cells and restores skin flexibility |
| Cremelin ® PURA (vegetable oils) (CREMER OLEO GmbH & Co. KG) | 1.00 | Natural petrolatum |
| Almond oil (*prunus amygdalus dulcis*) | 1.00 | Emollient |
| Olive oil (*olea europaea*) | 1.00 | Soothing, promotes oil spreading and skin smoothness |
| Jojoba oil (*simmondsia chinesis*) | 8.00 | Wax esters for antioxidant, moisture emollient, improves skin elasticity |
| Dow Corning ® 200, 100 cSt (dimethicone) (Dow Corning Corporation) | 0.50 | Silicone spreading |
| Freshcolat ® MGA (menthone glycerine acetal) (Symrise AG) | 1.00 | Skin coolant and refreshant |
| Triethanolamine 99% | 0.60 | pH adjustment |
| Escalol ® 557 Octinoxate (Ashland Inc.) | 1.00 | UV absorber |
| Germaben ® II (propylene glycol (and) diazolidinyl urea (and) methylparaben (and) propylparaben) (Sutton Laboratories) | 1.00 | Preservative |
| Phytotal ™ AI PS (glycerin, aqua, butylene glycol, *euphrasia officinalis* extract, *melissa officinalis* extract, *magnolia biondii* extract, lecithin) (Croda International PLC) | 2.30 | Reduces visible and physical signs of irritation |
| SymSitive ® 1609 (pentylene glycol, 4-t-butylcyclohexanol) (Symrise AG) | 3.00 | Reduces neuropathic pain (e.g., stinging and burning) |
| Cucumber phytobasic in glycerine (*cucumis sativa* extract) | 2.30 | Astringent/skin tightening |
| Pro-Lipo ™ Neo (propanediol (and) lecithin) (Unipex Group Inc.) | 1.30 | Pro-liposome encapsulation skin penetrant; increases skin penetration and bioavailability of entrapped hydrophilic |

TABLE 1-continued

| Ingredient | Weight Percent | Function |
| --- | --- | --- |
| | | and/or lipophilic active ingredients for better and faster results |

The cream 1440 can be infused or stored in a silicone (or similar) elastomer sheet or pad, which can be available in various sizes to use as a dressing over a surgical or traumatic scar. The cream 1440 can be located in a recessed compartment within the elastomer sheet or pad. The elastomer sheet or pad can be stored prior to clinical application by using an impermeable or semipermeable peel away covering. For example, the elastomer sheet or pad can be sized and shaped to fit over a caesarian section scar. The sheet or pad can be applied over the entire length of the scar for several weeks following the caesarian section procedure, allowing the scar (and the patient) to benefit from the cream contained in the sheet or pad. Additionally, the sheet or pad can retain moisture, which can soften a scar and protect the skin from post-surgical hypersensitivity.

Figure 15:
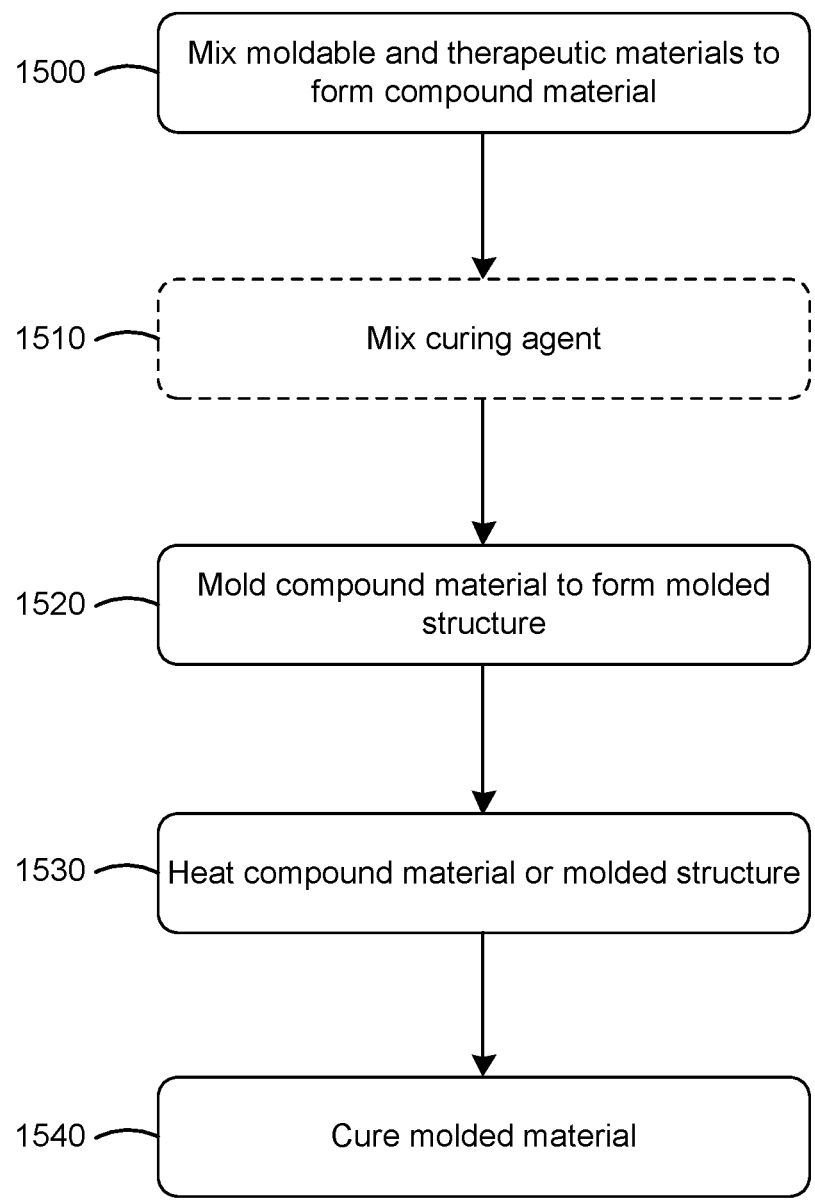
FIG. 15 is a flow chart of a method for manufacturing an apparatus for treating a dermatological condition such as scar tissue according to one or more embodiments.

FIG. 15 is a flow chart 15 of a method for manufacturing an apparatus for treating a dermatological condition such as scar tissue according to one or more embodiments. In step 1500, a moldable material and a therapeutic material are mixed to form a compound material. The moldable material can include any of the device materials described herein including silicone, fluoro-silicone, rubber, thermo-plastic rubber, polyurethane rubber, polyvinyl chloride (PVC), latex, polyisoprene, an elastomer, an elasto-plastic, or other plastic or polymeric materials. The therapeutic material can have one or more properties that can treat, heal, soothe, and/or provide another benefit for a dermatological condition or feature, such as scar tissue. For example, the therapeutic material can include a therapeutic cream or lotion, such as cream 1440 described below, a moisturizing cream or lotion (e.g., such as cream 1440 discussed below), an emollient, an emulsifier, an essential oil (or combination thereof), and/or another therapeutic material.

The compound material can have a weight or volume percentage of about 1% to about 20%, including about 5%, about 10%, about 15%, and any percentage or percentage range between any two of the foregoing percentages, of therapeutic material and a weight or volume percentage of about 80% to about 99% (by weight), including about 85%, about 90%, about 95%, and any percentage or percentage range between any two of the foregoing percentages, of moldable material. In a specific example, the compound material includes about 80% to about 99% (by weight) of silicone and about 1% to about 20% (by weight) of therapeutic cream (e.g., cream 1440). In another specific example, the compound material includes about 80% to about 99% (by volume) of silicone and about 1% to about 20% (by volume) of therapeutic cream (e.g., cream 1440).

In some embodiments, a curing agent is also mixed with the moldable and therapeutic materials to form the compound material in optional step 1510. The curing agent can include platinum, tin, a peroxide, and/or a photoinitiator. Examples of peroxides that can be used as curing agents include dicumyl peroxide and dichlorobenzoyl peroxide. The curing agent can correspond to the mold heating temperature (in step 1530) and the curing method (step 1540). For example, different curing agents can be heated to different temperatures in step 1530 and they can be cured by different curing methods in step 1540. In some embodiments, the amount of curing agent added to the compound material can be within the range of about 0.15% to about 3% by weight of the compound material.

The mixing in steps 1500 and 1510 can occur manually or automatically. In some embodiments, the mixing occurs automatically by pumping the constituent materials, at the desired weight percentages, into a static mixer In step 1520, the compound material is molded (e.g., injection or compression molded) to form a molded structure. The molded structure can have the same form as, substantially the same form as, or a different form than any of the devices described herein. For example, the molded structure can have a substantially cylindrically-shaped body having an axial length and a width and having a wall of a finite thickness, and defining a cylindrical cavity suited to receive a finger. The wall can have an interior surface defined by the cavity and an exterior surface. The molded structure can also have a textured region defined on at least a portion of the exterior surface of the body. The textured region can include raised features extending from the exterior surface of the body. The raised features can have an elongated shape can include first and second groups of raised features. The first group of raised features can be oriented in a first direction and the second group of raised features can be oriented in a second direction that is orthogonal to the first direction.

The compound material is heated prior to or during molding in step 1530. For example, the compound material and/or the molded structure can be heated to about 60° F. to about 120° F., about 100° F. to about 225° F., or about 300° F. to about 350° F. (e.g., as described above). In some embodiments, the heating temperature can correspond to the added curing agent (step 1510) and the curing method (step 1540).

In step 1540, the molded structure is cured. The curing step 1540 can include a platinum-based cure, which can occur when the curing agent includes platinum (e.g., a platinum-based catalyst or compound). In another example, the curing step 1540 can include a peroxide-based cure when the curing agent includes a peroxide. In another example, the curing step 1540 can include a tin-based cure when the curing agent includes tin (e.g., a tin-based catalyst or compound).

In one example, the curing step 1540 occurs as a result of using platinum or peroxide as the curing agent (step 1510) and heating the molded compound (or compound material) to a temperature within the range of about 300° F. to about 350° F. (in step 1530). In another example, the curing step 1540 occurs as a result of using platinum or tin as the curing agent (step 1510) and heating the molded compound (or compound material) to a temperature within the range of about 100° F. to about 225° F. in a room-temperature vulcanization curing process. In yet another example, the curing step includes exposing the molded structure to ultraviolet light and heating the molded compound (or compound material) to a temperature within the range of about 60° F. to about 120° F. in a UV curing process. UV curing can also include adding a curing agent (step 1510) such as platinum or a photoinitiator.

Figure 16:
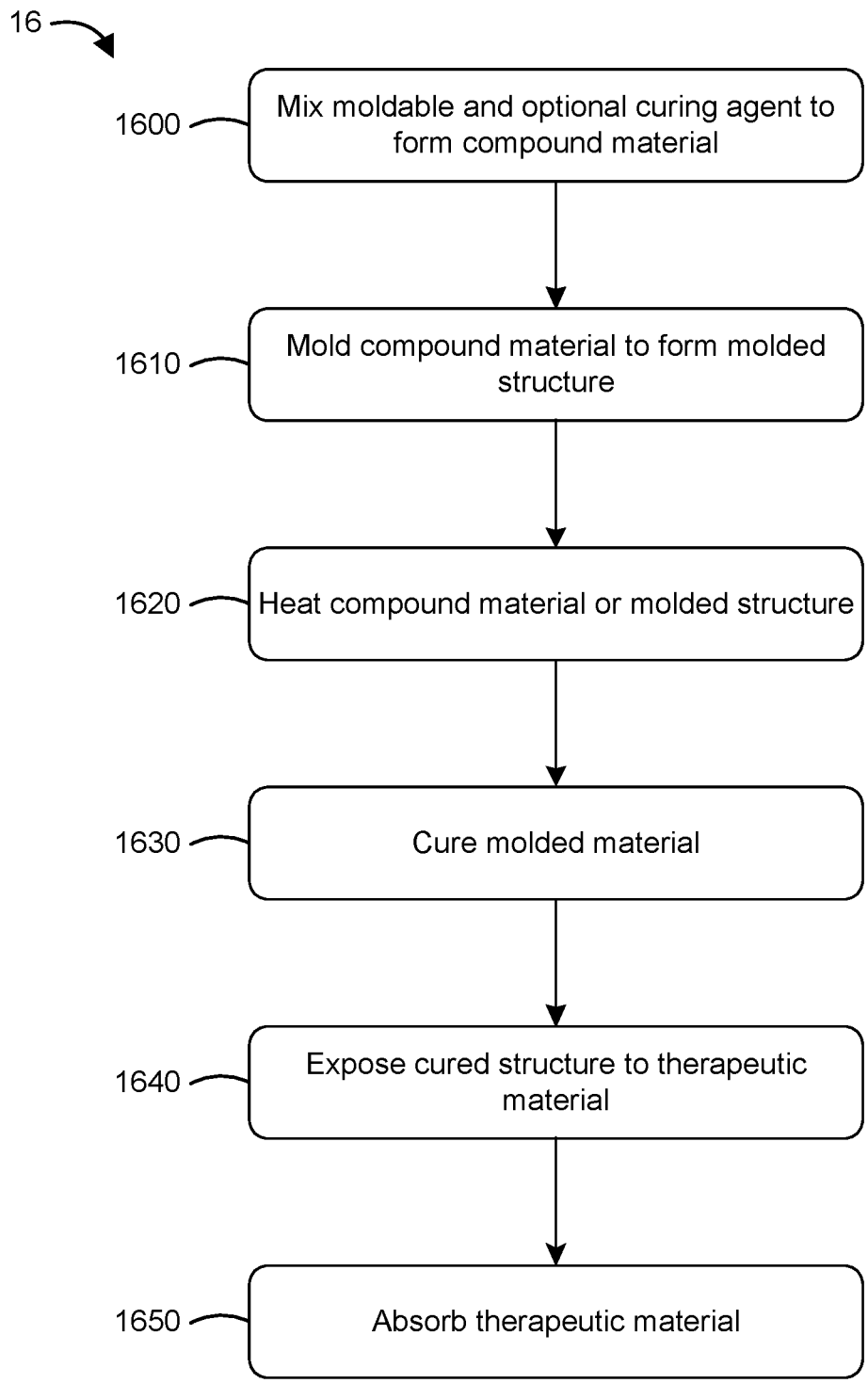
FIG. 16 is a flow chart of a method for manufacturing an apparatus for treating a dermatological condition such as scar tissue according to one or more alternative embodiments.

FIG. 16 is a flow chart 16 of a method for manufacturing an apparatus for treating a dermatological condition such as scar tissue according to one or more alternative embodiments. In step 1600, a moldable material and an optional curing agent are mixed together to form a compound material (e.g., as discussed above in steps 1500 and 1510). In step 1610, the compound material is molded to form a molded structure (e.g., as discussed above in step 1520). In step 1620, the compound material and/or the molded structure are heated prior to or during molding step 1610 (e.g., as discussed above in step 1530). In step 1630, the molded structure is cured (e.g., as discussed above in step 1540) to form a cured structure. In step 1640, the cured structure is exposed to the therapeutic material. For example, the therapeutic material can be in liquid form (e.g., a cream, a lotion, or other liquid) and the cured structure can be partially or fully submerged in the liquid therapeutic material. In step 1650, at least some of the therapeutic material is absorbed into the cured structure to form the device.

As a result of incorporating the therapeutic material into the device (e.g., in flow chart(s) 15 and/or 16), the device can have improved therapeutic benefits and can be more convenient for the user. For example, the device can release at least some of the incorporated therapeutic material when the device is heated (e.g., due to friction during use and/or by application of an external heat source). The device can release the therapeutic material from its external wall such that the therapeutic contacts the dermatological feature (e.g., scar tissue) while the device is being used on the dermatologic feature, which can enhance the device's therapeutic benefits compared to not using the therapeutic material. Also, since the device already has the therapeutic material incorporated, the user does not need to purchase or remember to use the therapeutic material lotion during treatment.

The present invention should not be considered limited to the particular embodiments described above, but rather should be understood to cover all aspects of the invention as fairly set out in the present claims. Various modifications, equivalent processes, as well as numerous structures to which the present invention may be applicable, will be readily apparent to those skilled in the art to which the present invention is directed upon review of the present disclosure. The claims are intended to cover such modifications.

What is claimed is:

1. An apparatus for treating skin, the apparatus comprising:
    a substantially cylindrically shaped body having an axial length and a width and having a wall of a finite thickness, and defining a cylindrical cavity suited to receive a finger, said wall having an interior surface defined by said cavity, as well as an exterior surface;
    said body further having a first end and a second end at opposing ends of said axial length of said body, said first end comprising an aperture to allow a finger to pass through said aperture and into the cavity along said axial length, and the interior surface of the second end conforms to a tip of a finger;
    said body additionally comprising at least one side opening in a side of said wall; and
    a textured region defined on at least a portion of the exterior surface of the body, the textured region comprising raised features extending from the exterior surface of the body, the raised features having an elongated shape, wherein a first group of the raised features is oriented in a first direction and a second group of the raised features is oriented in a second direction, the second direction orthogonal to the first direction,
    wherein the body is formed by a molded compound material that includes a therapeutic material and a moldable material,
    wherein the therapeutic material comprises a therapeutic cream configured to treat scar tissue.

2. The apparatus of claim 1, wherein the compound material is configured to release a portion of the therapeutic material when heated above room temperature.

3. The apparatus of claim 1, wherein the textured region includes a grid having a first section comprised of the first group of the raised features and a second section comprised of the second group of the raised features, the first section adjacent to the second section.

4. The apparatus of claim 1, wherein the moldable material comprises silicone.

5. The apparatus of claim 1, wherein the molded compound material includes a range of about 1% by weight to about 15% by weight of the therapeutic material and a range of about 85% by weight to about 99% by weight of the moldable material.

6. A method for manufacturing an apparatus, comprising:
mixing a therapeutic material and a moldable material to form a mixed material, the therapeutic material for treating a dermatological condition;
molding the mixed material to form a molded structure that comprises:
a substantially cylindrically-shaped body having an axial length and a width and having a wall of a finite thickness, and defining a cylindrical cavity suited to receive a finger, said wall having an interior surface defined by said cavity, as well as an exterior surface; and
a textured region defined on at least a portion of the exterior surface of the body, the textured region comprising raised features extending from the exterior surface of the body, the raised features having an elongated shape, wherein a first group of the raised features is oriented in a first direction and a second group of the raised features is oriented in a second direction, the second direction orthogonal to the first direction; and
curing the molded structure to form the apparatus,
wherein the therapeutic material comprises a therapeutic cream configured to treat scar tissue.

7. The method of claim 6, further comprising mixing a curing agent with the therapeutic material and the moldable material.

8. The method of claim 7, wherein the curing agent comprises platinum or a peroxide.

9. The method of claim 8, wherein the molding step includes heating the mixed material to a temperature within a range of about 300° F. to about 350° F.

10. The method of claim 7, wherein the curing agent comprises platinum or tin.

11. The method of claim 10, wherein the molding step includes heating the mixed material to a temperature within a range of about 100° F. to about 225° F.

12. The method of claim 6, wherein the molding step includes heating the mixed material to a temperature within a range of about 60° F. to about 120° F. and the curing step includes exposing the molded structured to ultraviolet light.

13. The method of claim 6, further comprising mixing the therapeutic material and the moldable material in a static mixer.

14. The method of claim 13, further comprising pumping the therapeutic material and the moldable material into the static mixer.

15. The method of claim 6, wherein the moldable material comprises silicone.

16. The method of claim 6, wherein the molding step includes injection molding or compression molding.

* * * * *